(12) United States Patent
Chauhan et al.

(10) Patent No.: US 9,642,925 B2
(45) Date of Patent: May 9, 2017

(54) MAGNETIC NANOPARTICLE FORMULATIONS, METHODS FOR MAKING SUCH FORMULATIONS, AND METHODS FOR THEIR USE

(75) Inventors: Subhash Chauhan, Sioux Falls, SD (US); Meena Jaggi, Sioux Falls, SD (US); Murali Mohan Yallapu, Sioux Falls, SD (US)

(73) Assignee: Sanford Research/USD, Sioux Falls, SD (US)

( * ) Notice: Subject to any disclaimer, the term of this patent is extended or adjusted under 35 U.S.C. 154(b) by 719 days.

(21) Appl. No.: 13/884,625

(22) PCT Filed: Feb. 7, 2011

(86) PCT No.: PCT/US2011/063723
§ 371 (c)(1),
(2), (4) Date: May 15, 2013

(87) PCT Pub. No.: WO2012/078745
PCT Pub. Date: Jun. 14, 2012

(65) Prior Publication Data
US 2013/0245357 A1 Sep. 19, 2013

Related U.S. Application Data

(60) Provisional application No. 61/420,664, filed on Dec. 7, 2010.

(51) Int. Cl.
| | |
|---|---|
| A61K 49/18 | (2006.01) |
| H01F 1/00 | (2006.01) |
| A61K 41/00 | (2006.01) |
| A61K 9/51 | (2006.01) |
| A61K 31/12 | (2006.01) |
| A61N 2/00 | (2006.01) |
| B82Y 25/00 | (2011.01) |

(52) U.S. Cl.
CPC ........ *A61K 49/1824* (2013.01); *A61K 9/5161* (2013.01); *A61K 9/5192* (2013.01); *A61K 31/12* (2013.01); *A61K 41/0052* (2013.01); *A61K 41/0057* (2013.01); *A61K 49/1845* (2013.01); *A61K 49/1857* (2013.01); *A61N 2/002* (2013.01); *H01F 1/0054* (2013.01); *B82Y 25/00* (2013.01)

(58) Field of Classification Search
None
See application file for complete search history.

(56) References Cited

PUBLICATIONS

Hou et al. Inorganic nanocrystal self-assembly via the inclusion interaction of beta-cyclodextrins: toward 3D spherical magnetite. 2005 J. Phys. Chem. B. 109: 4845-4852.*
Davis ME. The first targeted delivery of siRNA in humans via a self-assembling, cyclodextrin polymer-based nanoparticle: from concept to clinic. 2009 Mol. Pharm. 6: 659-668. Published online Mar. 6, 2009.*
Brasseur et al. Water-soluble aluminium phthalocyanine-polymer conjugates for PDT: photodynamic activities and pharmacokinetics in tumour-bearing mice. 1999 Br. J. Cancer 80: 1533-1541.*
Lu AH, Salabas EL, Schuth F. Magnetic nanoparticles: synthesis, protection, functionalization, and application. Angew Chem Int Ed Engl 2007;46:1222-44.
Ito A, Shinkai M, Honda H, Kobayashi T. Medical application of functionalized magnetic nanoparticles. J Biosci Bioeng 2005;100:1-11.
Saiyed Z, Telang S, Ramchand C. Application of magnetic techniques in the field of drug discovery and biomedicine. Biomagn Res Technol 2003;1:2.
Zhang L, Yu F, Cole AJ, Chertok B, David AE, Wang J, et al. Gum arabic-coated magnetic nanoparticles for potential application in simultaneous magnetic targeting and tumor imaging. Aaps J 2009;11:693-9.
Johannsen M, Gneveckow U, Eckelt L, Feussner A, Waldofner N, Scholz R, et al. Clinical hyperthermia of prostate cancer using magnetic nanoparticles: presentation of a new interstitial technique. Int J Hyperthermia 2005;21:637-47.
Sun C, Lee JS, Zhang M. Magnetic nanoparticles in MR imaging and drug delivery. Adv Drug Deliv Rev 2008;60:1252-65.
Kohler N, Sun C, Fichtenholtz A, Gunn J, Fang C, Zhang M. Methotrexate-immobilized poly(ethylene glycol) magnetic nanoparticles for MR imaging and drug delivery. Small 2006;2:785-92.
Bruce IJ, Sen T. Surface modification of magnetic nanoparticles with alkoxysilanes and their application in magnetic bioseparations. Langmuir 2005;21:7029-35.
Wilhelm C, Gazeau F. Universal cell labelling with anionic magnetic nanoparticles. Biomaterials 2008;29:3161-74.
Lee SY, Harris MT. Surface modification of magnetic nanoparticles capped by oleic acids: characterization and colloidal stability in polar solvents. J Colloid Interface Sci 2006;293:401-8.
Hoehn M, Kustermann E, Blunk J, Wiedermann D, Trapp T, Wecker S, et al. Monitoring of implanted stem cell migration in vivo: a highly resolved in vivo magnetic resonance imaging investigation of experimental stroke in rat. Proc Natl Acad Sci U S A 2002;99:16267-72.
Montet-Abou K, Montet X, Weissleder R, Josephson L. Cell internalization of magnetic nanoparticles using transfection agents. Mol Imaging 2007;6:1-9.
McCarthy JR, Weissleder R. Multifunctional magnetic nanoparticles for targeted imaging and therapy. Adv Drug Deliv Rev 2008;60:1241-51.
Guthi JS, Yang SG, Huang G, Li S, Khemtong C, Kessinger CW, et al. MRI-visible micellar nanomedicine for targeted drug delivery to lung cancer cells. Mol Pharm 2010;7:32-40.
Cinteza LO, Ohulchanskyy TY, Sahoo Y, Bergey EJ, Pandey RK, Prasad PN. Diacyllipid micelle-based nanocarrier for magnetically guided delivery of drugs in photodynamic therapy. Mol Pharm 2006;3:415-23.
Pradhan P, Giri J, Rieken F, Koch C, Mykhaylyk O, Doblinger M, et al. Targeted temperature sensitive magnetic liposomes for thermo-chemotherapy. J Control Release142:108-21, 2010.
Shubayev VI, Pisanic TR, 2nd, Jin S. Magnetic nanoparticles for theragnostics. Adv Drug Deliv Rev 2009;61:467-77.
Rubio-Retama J, Zafeiropoulos NE, Serafinelli C, Rojas-Reyna R, Voit B, Cabarcos EL, et al. Synthesis and characterization of thermosensitive PNIPAM microgels covered with superparamagnetic gamma-Fe2O3 nanoparticles. Langmuir 2007;23:10280-5.

(Continued)

*Primary Examiner* — Michael G Hartley
*Assistant Examiner* — Jennifer Lamberski
(74) *Attorney, Agent, or Firm* — McDonnell Boehnen Hulbert & Berghoff LLP

(57) ABSTRACT

The present invention provides derivatized magnetic nanoparticles, methods for making such nanoparticles, and methods for their use.

19 Claims, 15 Drawing Sheets

(56) References Cited

PUBLICATIONS

Wang L, Yang Z, Zhang Y, Wang L. Biofunctional nanoparticles with magnetization and luminescence. J Phys Chem C 2009;113:3955-9.

Guo R, Zhang L, Qian H, Li R, Jiang X, Liu B. Multifunctional nanocarriers for cell imaging, drug delivery, and near-IR photothermal therapy. Langmuir 2010;26:5428-34.

Yallapu MM, Foy SP, Jain TK, Labhasetwar V. PEG-Functionalized Magnetic Nanoparticles for Drug Delivery and Magnetic Resonance Imaging Applications. Pham Res 2010. DOI: 10.1007/s11095-010-0260-1.

Jain TK, Reddy MK, Morales MA, Leslie-Pelecky DL, Labhasetwar V. Biodistribution, clearance, and biocompatibility of iron oxide magnetic nanoparticles in rats. Mol Pharm 2008;5:316-27.

Gao J, Gu H, Xu B. Multifunctional magnetic nanoparticles: design, synthesis, and biomedical applications. Acc Chem Res 2009;42:1097-107.

Banerjee SS, Chen D-H. Magnetic Nanoparticles Grafted with Cyclodextrin for Hydrophobic Drug Delivery. Chem Mater 2007;19:6345-9.

Bhattarai SR, Kc RB, Kim SY, Sharma M, Khil MS, Hwang PH, et al. N-hexanoyl chitosan stabilized magnetic nanoparticles: Implication for cellular labeling and magnetic resonance imaging. J Nanobiotechnology 2008;6:1.

Yallapu MM, Maher DM, Sundram V, Bell MC, Jaggi M, Chauhan SC. Curcumin induces chemo/radio-sensitization in ovarian cancer cells and curcumin nanoparticles inhibit ovarian cancer cell growth. J Ovarian Res 2010;3:11.

Luo B, Song XJ, Zhang F, Xia A, Yang WL, Hu JH, et al. Multi-functional thermosensitive composite microspheres with high magnetic susceptibility based on magnetite colloidal nanparticle clusters. Langmuir 2010;26:1674-9.

Beaven GH, Chen S-H, D'albis A, Gratzer WB. A spectroscopic study of the haemin-human-serum-albumin system. Eur J Biochem 1974;41:539-46.

Chipman DM, Grisaro V, NSharon N. The binding of oligosaccharides containing N-acetylglucosamin and N-acetylmuramic acid to lysozyme. J Biol Chem 1967;242:4388-94.

Chauhan SC, Vannatta K, Ebeling MC, Vinayek N, Watanabe A, Pandey KK, et al. Expression and functions of transmembrane mucin MUC13 in ovarian cancer. Cancer Res 2009;69:765-74.

Lim JK, Majetich SA, Tilton RD. Stabilization of superparamagnetic iron oxide core-gold shell nanoparticles in high ionic strength media. Langmuir 2009;25:13384-93.

Lin JJ, Chen JS, Huang SJ, Ko JH, Wang YM, Chen TL, et al. Folic acid-Pluronic F127 magnetic nanoparticle clusters for combined targeting, diagnosis, and therapy applications. Biomaterials 2009;30:5114-24.

Xiong XY, Tam KK, Gan LH. Release kinetics of hydrophobic and hydrophilic model drugs from pluronic F127/poly (lactic acid) nanoparticles. J Control Release 2005;103:73-82.

Dorris A, Rucareanu S, Reven L, Barrett CJ, Lennox RB. Preparation and characterization of polyelectrolyte-coated gold nanoparticles. Langmuir 2008;24:2532-8.

Latham AH, Williams ME. Controlling transport and chemical functionality of magnetic nanoparticles. Acc Chem Res 2008;41:411-20.

Peracchia MT, Vauthier C, Puisieux F, Couvreur P. Development of sterically stabilized poly(isobutyl 2-cyanoacrylate) nanoparticles by chemical coupling of poly-ethylene glycol). J Biomed Mater Res 1997;34:317-26.

Gupta AK, Gupta M. Synthesis and surface engineering of iron oxide nanoparticles for biomedical applications. Biomaterials 2005;26:3995-4021.

Billotey C, Wilhelm C, Devaud M, Bacri JC, Bittoun J, Gazeau F. Cell internalization of anionic maghemite nanoparticles: quantitative effect on magnetic resonance imaging. Magn Reson Med 2003;49:646-54.

Yallapu MM, Gupta BK, Jaggi M, Chauhan SC. Fabrication of curcumin encapsulated PLGA nanoparticles for improved therapeutic effects in metastatic cancer cells. J Colloid Interface Sci 2010.

Salomir R, Vimeux FC, de Zwart JA, Grenier N, Moonen CT. Hyperthermia by MR-guided focused ultrasound: accurate temperature control based on fast MRI and a physical model of local energy deposition and heat conduction. Magn Reson Med 2000;43:342-7.

Salomir R, Palussiere J, Vimeux FC, de Zwart JA, Quesson B, Gauchet M, et al. Local hyperthermia with MR-guided focused ultrasound: spiral trajectory of the focal point optimized for temperature uniformity in the target region. J Magn Reson Imaging 2000;12:571-83.

Le Renard PE, Jordan O, Faes A, Petri-Fink A, Hofmann H, Rufenacht D, et al. The in vivo performance of magnetic particle-loaded injectable, in situ gelling, carriers for the delivery of local hyperthermia. Biomaterials 2010;31:691-705.

Le Renard PE, Buchegger F, Petri-Fink A, Bosman F, Rufenacht D, Hofmann H, et al. Local moderate magnetically induced hyperthermia using an implant formed in situ in a mouse tumor model. Int J Hyperthermia 2009;25:229-39.

Gentilini C, Evangelista F, Rudolf P, Franchi P, Lucarini M, Pasquato L. Water-soluble gold nanoparticles protected by fluorinated amphiphilic thiolates. J Am Chem Soc 2008;130:15678-82.

Latorre M, Rinaldi C. Applications of magnetic nanoparticles in medicine: magnetic fluid hyperthermia. P R Health Sci J 2009;28:227-38.

Duguet E, Vasseur S, Mornet S, Devoisselle JM. Magnetic nanoparticles and their applications in medicine. Nanomedicine 2006;1:157-68.

Xia H-B, Yi J, Foo P-S, Liu B. Facile fabrication of water-soluble magnetic nanoparticles and their spherical aggregates. Chem Mater 2007;19:4087-91.

Kato H, Ishida T. Present and future status of noninvasive selective deep heating using RF in hyperthermia. Med Biol Eng Comput 1993;31 Suppl:S2-11.

Motoyama J, Hakata T, Kato R, Yamashita N, Morino T, Kobayashi T, et al. Size dependent heat generation of magnetite nanoparticles under AC magnetic field for cancer therapy. Biomagn Res Technol 2008;6:4.

Deger S, Taymoorian K, Boehmer D, Schink T, Roigas J, Wille AH, et al. Thermoradiotherapy using interstitial self-regulating thermoseeds: an intermediate analysis of a phase II trial. Eur Urol 2004;45:574-9; discussion 80.

Kawashita M, Tanaka M, Kokubo T, Inoue Y, Yao T, Hamada S, et al. Preparation of ferrimagnetic magnetite microspheres for in situ hyperthermic treatment of cancer. Biomaterials 2005;26:2231-8.

Serrano MC, Portoles MT, Pagani R, de Guinoa JS, Ruiz-Hernandez E, Arcos D, et al. In vitro positive biocompatibility evaluation of glass-glass ceramic thermoseeds for hyperthermic treatment of bone tumors. Tissue Eng Part A 2008;14:617-27.

Liong M, Lu J, Kovochich M, Xia T, Ruehm SG, Nel AE, et al. Multifunctional inorganic nanoparticles for imaging, targeting, and drug delivery. ACS Nano 2008;2:889-96.

Orrenius S, Zhivotovsky B. The future of toxicology—Does it matter how cells die? Chem Res Toxicol 2006;19:729-33.

Malugin A, Kopeckova P, Kopecek J. HPMA copolymer-bound doxorubicin induces apoptosis in ovarian carcinoma cells by the disruption of mitochondrial function. Mol Pharm 2006;3:351-61.

McGowan AJ, Ruiz-Ruiz MC, Gorman AM, Lopez-Rivas A, Cotter TG. Reactive oxygen intermediate(s) (ROI): common mediator(s) of poly(ADP-ribose)polymerase (PARP) cleavage and apoptosis. FEBS Lett 1996;392:299-303.

de Murcia G, Menissier de Murcia J. Poly(ADP-ribose) polymerase: a molecular nick-sensor. Trends Biochem Sci 1994;19:172-6.

Liu F, Park JY, Zhang Y, Conwell C, Liu Y, Bathula SR, Huang L. Targeted cancer therapy with novel high drug-loading nanocrystals. J Pharm Sci 2010;99:3542-3551.

Rodriguez-Perez, et al., (2006) "Drug solubilization and delivery from cyclodextrin-pluronic aggregates," Journal of Nanoscience and Nanotechnology, 6:3179-3186.

Namdeo M, Saxena S, Tankhiwale R, Bajpai M, Mohan YM, Bajpai SK. Magnetic nanoparticles for drug delivery applications. J Nanosci Nanotechnol 2008;8:3247-71.

(56) References Cited

OTHER PUBLICATIONS

Wilhelm C, Fortin JP, Gazeau F. Tumour cell toxicity of intracellular hyperthermia mediated by magnetic nanoparticles. J Nanosci Nanotechnol 2007;7:2933-7.

Osaka T, Matsunaga T, Nakanishi T, Arakaki A, Niwa D, Iida H. Synthesis of magnetic nanoparticles and their application to bioassays. Anal Bioanal Chem 2006;384:593-600.

Dey T. Polymer-coated magnetic nanoparticles: surface modification and end-functionalization. J Nanosci Nanotechnol 2006; 6:2479-83.

Gupta AK, Naregalkar RR, Vaidya VD, Gupta M. Recent advances on surface engineering of magnetic iron oxide nanoparticles and their biomedical applications. Nanomedicine 2007;2:23-39.

Flexman JA, Minoshima S, Kim Y, Cross DJ. Magneto-optical labeling of fetal neural stem cells for in vivo MRI tracking. Conf Proc IEEE Eng Med Biol Soc 2006;1:5631-4.

Bae KH, Ha YJ, Kim C, Lee KR, Park TG. Pluronic/chitosan shell cross-linked nanocapsules encapsulating magnetic nanoparticles. J Biomater Sci Polym Ed 2008;19:1571-83.

Smirnov P. Cellular magnetic resonance imaging using superparamagnetic anionic iron oxide nanoparticles: applications to in vivo trafficking of lymphocytes and cell-based anticancer therapy. Methods Mol Biol 2009;512:333-53.

Jain, et al., (2005) "Iron oxide nanoparticles for sustained delivery of anticancer agents," Molecular Pharmaceutics, 2:194-205.

Qin, et al., (2007) "A high-performance magnetic resonance imaging T2 contrast agent," Advanced Materials, 19(14): 1874-1878.

Cobos Cruz, et al. (2008) "Synthesis of magnetite nanoparticles-beta-cyclodextrin complex," Journal of Alloys and Compounds, 466(1-2):330-334.

Yallapu, et al., (2010) "[beta]-cyclodextrin-curcumin self-assembly enhances curcumin delivery in prostate cancer cells," Colloids and Surfaces B: Biointerfaces, 79(1): 113-125.

Yallapu, et al., (2010) "Multi-functional magnetic nanoparticles for magnetic resonance imaging and cancer therapy," Biomaterials, 32(7): 1890-1905.

International Search Report PCT/US2011/063723, mailed Apr. 11, 2012.

* cited by examiner

MAGNETIC NANOPARTICLE FORMULATIONS, METHODS FOR MAKING SUCH FORMULATIONS, AND METHODS FOR THEIR USE

CROSS REFERENCE

This application claims priority to U.S. Provisional Patent Application Ser. No. 61/420,664 filed Dec. 7, 2010, incorporated by reference herein in its entirety.

STATEMENT OF U.S. GOVERNMENT SUPPORT

This work was supported by Department of Defense Grants PC073887 and PC073643, and NIH RO1 grant number CA142736. The U.S. government has certain rights in the invention.

BACKGROUND

Magnetic nanoparticles (MNPs) have potential for a number of biomedical applications due to their inherent ultra fine size, biocompatibility and superparamagnetic properties. However, conventional iron oxide nanoformulations stabilized by natural/synthetic polymer or encapsulated in micro/nanogels, colloidosome/liposome, micelles, microcapsules, or transfecting reagents (cationic lipids, polylysine, and protamine sulfate), etc. have exhibited poor efficacy of drug loading or rapid release of drug molecules, loss of magnetization properties and often increase the particle size of the formulation. Some of these complexes are unstable and tend to aggregate in reaction tubes or even precipitate in the cell culture medium, resulting in cytotoxicity. Such formulations eventually lead to rapid clearance from the body's circulation by the reticuloendothelial system (RES) and limit the efficacy of magnetic nanoparticle-mediated drug targeting ability. Limited efforts have been made toward developing a universal combined formulation for cancer applications. Therefore, developing a multi-functional magnetic nanoparticle formulation which does not compromise basic characteristics is highly desirable.

SUMMARY OF THE INVENTION

In a first aspect, the present invention provides magnetic nanoparticles (MNP) comprising
 (a) a core MNP;
 (b) first layer of cyclodextrin over the core MNP; and
 (c) a second layer of a pluronic polymer over the cyclodextrin layer.

In one embodiment, the core MNP comprises iron, nickel, cobalt, or derivatives thereof. In a further embodiment, the core MNP comprises iron oxide. In another embodiment, the core MNP is between about 5 nm and about 30 nm in diameter.

The invention also provides MNP clusters, comprising a plurality of MNPs according to any embodiment or combination of embodiments of the invention, wherein the MNP clusters are between about 50 nm and about 200 nm in diameter.

In one embodiment, the cyclodextrin is selected from the group consisting of α-cyclodextrin, β-cyclodextrin, and γ-cyclodextrin, and derivatives thereof. In a further embodiment, the MNPs comprise a molar ratio of between about 1:40 to 1:300 cyclodextrin:metal ion in the core MNP. In another embodiment, the pluronic polymer comprises an ethylene oxide/propylene oxide block copolymer. In a still further embodiment, the MNPs comprise a molar ratio of between about 1:1 and 1:10 cyclodextrin:pluronic polymer.

In various embodiments, the MNPs or MNP clusters further comprise one or more of a therapeutic loaded into or onto the MNP, a cell-targeting compound bound to the MNP, and a photosensitizer loaded into or onto the MNP.

The invention also provides pharmaceutical compositions, comprising MNPs or MNP clusters of any embodiment or combination of embodiments of the invention, and a pharmaceutically acceptable carrier.

The invention further provides methods for making magnetic nanoparticles, comprising
 (a) precipitation of metal salts in the presence of ammonia to obtain metal oxide core nanoparticles; and
 (b) coating the metal oxide core nanoparticles with:
  (i) cyclodextrin; and
  (ii) a pluronic polymer.

In one embodiment, the core MNP comprises iron, nickel, cobalt, or derivatives thereof. In a further embodiment, the core MNP comprises iron oxide. In another embodiment, the core MNP is between about 5 nm and about 30 nm in diameter. In a further embodiment, the cyclodextrin is selected from the group consisting of α-cyclodextrin, β-cyclodextrin, and γ-cyclodextrin, and derivatives thereof. In another embodiment, the MNPs comprise a molar ratio of between about 1:40 to 1:300 cyclodextrin:metal ion in the core MNP. In a further embodiment, the pluronic polymer comprises an ethylene oxide/propylene oxide block copolymer. In a still further embodiment, the MNPs comprise a molar ratio of between about 1:1 and 1:10 cyclodextrin:pluronic polymer.

In various embodiments, the methods further comprise loading one or more of a therapeutic, a cell-targeting compound, and a photosensitizer into or onto the MNP.

In another aspect, the present invention provides methods for drug delivery, comprising administering the MNP, MNP cluster, or pharmaceutical composition of any embodiment or combination of embodiments of the invention where a drug is loaded into the MNP, to a subject in need thereof.

In another aspect, the present invention provides methods for hyperthermic tumor treatment, comprising
 (a) administering the MNP, MNP cluster, or pharmaceutical composition of any embodiment or combination of embodiments of the invention, to a subject in need thereof so as to localize the MNP or MNP cluster to the vicinity of a tissue of interest, and
 (b) applying an alternating magnetic field to produce heat from the MNP or MNP cluster in the formulation;
 wherein the heat produced from the MNP or MNP cluster damages cells in the tissue and/or sensitize cells in the tissue to other therapy.

In another aspect, the invention provides methods for photodynamic treatment (PDT), comprising
 (a) administering the MNP, MNP cluster, or pharmaceutical composition of any embodiment or combination of embodiments of the invention, wherein the MNP comprise a photosensitizer, to a subject in need of PDT; and
 (b) applying a light source to excite the photosensitizer;
 wherein the excitation of the photosensitizer produces reactive oxygen species that damage cells in the relevant tissue.

In a further aspect, the invention provides methods for in vivo imaging comprising
 (a) administering the MNP, MNP cluster, or pharmaceutical composition of any embodiment or combination of embodiments of the invention, to a subject in need of magnetic resonance imaging; and (b) conducting magnetic resonance imaging (MRI) on the subject;

wherein the MRI permits in vivo imaging of the relevant tissue.

Tumor volume was monitored bi-weekly to determine inhibitory effect of vehicle, free curcumin, blank MNP and MNP-curcumin formulation.

Figure 15:
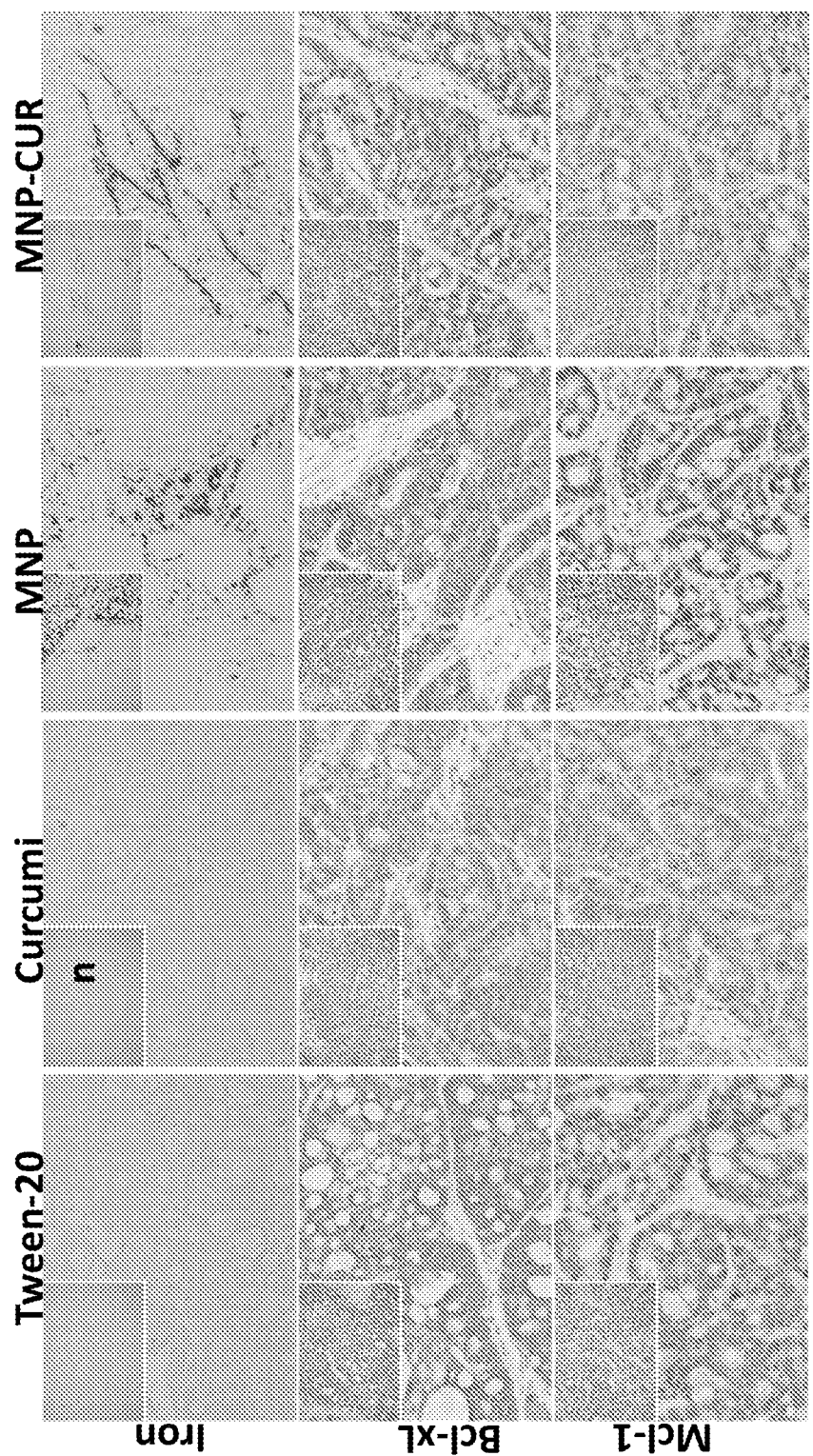

FIG. 15. The effect of MNP-curcumin formulation on the expression of Bcl-xL and MCL-1 oncogenes in pancreatic tumor xenografts. Pancreatic tumor xenografts were generated in athymic nude mice by subcutaneous (sc) injection of HPAFII human pancreatic cancer cells. Free curcumin or MNP-curcumin formulation was administered intra-tumorally at day 20 post-injection of tumor cells. Immunohistichemical (IHC) analysis was performed to determine the effect of vehicle (Tween-20), free curcumin, blank MNP and MNP-curcumin formulation on Bcl-xL and MCL-1 oncogenes expression. The presence of MNPs (iron) in tumors was determined by Prussian Blue staining. Original Magnifications 200×.

DETAILED DESCRIPTION OF THE INVENTION

All references cited are herein incorporated by reference in their entirety. As used herein, the singular forms "a", "an" and "the" include plural referents unless the context clearly dictates otherwise. "And" as used herein is interchangeably used with "or" unless expressly stated otherwise. All embodiments within and between different aspects of the invention can be combined unless the context clearly dictates otherwise.

In a first aspect, the present invention provides magnetic nanoparticles comprising
(a) a core magnetic nanoparticle;
(b) first layer of cyclodextrin over the core magnetic nanoparticle; and
(c) a second layer of a pluronic polymer over the cyclodextrin layer.

As disclosed herein, the magnetic nanoparticles ("MNPs") of the invention, and clusters thereof, significantly improve upon existing nanoparticle formulations by offering improved stability, enhanced cellular uptake, sustained release, reduced particle cluster size, and haemocompatibility, making them especially suitable for a wide variety of biomedical applications, including but not limited to drug delivery, in vivo imaging, hyperthermia applications, MRI visible targeting, photodynamic therapy, and chemotherapy.

As used herein, a "core MNP" means a class of nanoparticle which can be manipulated using magnetic field. Any suitable MNP may be used, including but not limited to iron, nickel and/or cobalt-based MNPs, including but not limited to oxides thereof. In one preferred embodiment, the MNP comprises an iron-based nanoparticle, such as an iron oxide nanoparticle; such MNPs are especially preferred for applications in which the MNP will be administered and subject to the body's metabolic processes. In a further preferred embodiment, the iron oxide nanoparticle comprises $Fe^{3+}$ and/or $Fe^{2+}$ ions; when used in combination, it is further preferred that the molar ratio be between about 3:1 and 1:1 $Fe^{3+}$ to $Fe^{2+}$ ions; more preferably about 2:1 $Fe^{3+}$ and/or $Fe^{2+}$ ions. Methods for preparing MNPs are known in the art. Any suitable method for making such MNPs can be used, including but not limited to co-precipitation, thermal decomposition, microemulsion, flame spray synthesis, and the methods disclosed herein.

In one preferred embodiment, individual core MNPs are between about 5 nm and about 30 nm in diameter; in various other embodiments, between about 5-25, 5-20, 2-15, 5-10, 7.5-30, 7.5-25, 7.5-20, 7.5-15, 10-30, 10-25, 10-20, 10-15, 15-30, 15-25, 15-20, 20-30, or 20-25 nm in diameter. As shown herein, surface functionalization of the core MNP with cyclodextrin and pluronic polymer layers not only coat the core magnetic nanoparticle, but also attenuate their cluster behavior in aqueous media, resulting in smaller MNP cluster sizes compared to previous MNPs, thus making them more suitable for biomedical applications. Thus, in another preferred embodiment, the MNP comprises an MNP cluster of 200 nm or less in diameter; preferably between about 50 nm and 200 nm in diameter. In various preferred embodiments, the MNP clusters are between about 75-200; 90-200; 100-200; 75-175; 90-175; 100-175; 75-150; 90-150; 100-150; 75-125; 90-125; 100-125; 75-110; or 90-110 nm in diameter.

In another preferred embodiment, the MNP/MNP clusters of the invention have a negative zeta potential value, which helps repel each MNP in a cluster, improving long-term stability and limiting the MNP cluster sizes. In a preferred embodiment, the negative zeta potential is between about −2 mV and about −11 mV. The zeta potential of the MNPs/MNP clusters can be determined using standard methods, such as those disclosed herein.

The MNPs of the invention comprise a first layer of cyclodextrin over a core MNP. Cyclodextrins are composed of 5 or more α-D-glucopyranoside units linked 1->4. Any suitable cyclodextrin can be used. In various preferred embodiments, the cyclodextrins are selected from the group consisting of α-cyclodextrin (six membered sugar ring molecule), β-cyclodextrin (seven sugar ring molecule), and γ-cyclodextrin (eight sugar ring molecule), and derivatives thereof. In a further preferred embodiment, the cyclodextrin comprises β-cyclodextrin, or derivatives thereof. Cyclodextrins are commercially available and can be made by means known in the art. Any suitable means for forming a layer of cyclodextrin on the MNP can be used, including but not limited to those disclosed below.

Cyclodextrins contain a series of hydrophilic hydroxyl groups, which can bind to the MNP surface, and present a hydrophobic cavity suitable for loading a compound of interest. The cyclodextrin can be topologically represented as cone-shaped with the larger and the smaller openings of the cone exposing to the solvent secondary and primary hydroxyl groups respectively. As a result, the interior of the cones are considerably less hydrophilic than the aqueous environment and able to host other hydrophobic molecules, while the exterior is sufficiently hydrophilic to impart cyclodextrin complexes water solubility. Cyclodextrins can thus form inclusion complexes with compounds of interest, which can penetrate body tissues and controllably release of the active compounds.

As shown in the examples that follow, the capacity of the MNPs to load a compound of interest continuously increased as the amount of cyclodextrin used for MNP coating increased. Thus, any suitable amount of cyclodextrin can be used that can result in MNPs, and clusters thereof, of a size suitable for an intended use, such as the preferred MNP/MNP clusters disclosed above. In various embodiments, the MNPs comprise a molar ratio of between about 1:40 to 1:300 cyclodextrin:metal ion in the core MNP. In various further embodiments, the MNPs comprise a molar ratio of between about 1:40 to 1:250; 1:40 to 1:200; 1:40 to 1:150; 1:40 to 1:100; 1:40 to 1:80; 1:80 to 1:300; 1:100 to 1:300; 1:150 to 1:300; 1:200 to 1:300; or 1:250 to 1:300 cyclodextrin:metal ion in the core MNP.

The MNPs of the invention comprise a second layer of a pluronic polymer over the cyclodextrin layer. Pluronic polymers ("poloxamers") are nonionic triblock copolymers composed of a central hydrophobic chain of polyoxypropylene (poly(propylene oxide)) (PPO) flanked by two hydrophilic chains of polyoxyethylene (poly(ethylene oxide)) (PEO). The hydrophobic PPO chain binds to the hydrophobic cavities of cyclodextrin and the hydrophilic PEO chain provides additional hydrophilicity and stability to the overall formulation. Thus, the MNP formulations comprise a magnetic core nanoparticle derivatized with hydrophobic and hydrophilic layers.

Because the lengths of the polymer blocks can be customized, many different poloxamers exist that have slightly different properties. For the generic term "poloxamer", these copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic tradename, coding of these copolymers starts with a letter to define its physical form at room temperature (L=liquid, P=paste, F=flake (solid)) followed by two or three digits, The first digit (two digits in a three-digit number) in the numerical designation, multiplied by 300, indicates the approximate molecular weight of the hydrophobe; and the last digit×10 gives the percentage polyoxyethylene content (e.g., L61=Pluronic with a polyoxypropylene molecular mass of 1,800 g/mol and a 10% polyoxyethylene content). In one preferred embodiment, the pluronic polymer comprises an ethylene oxide/propylene oxide block copolymer. Pluronic polymers are commercially available, and methods for their synthesis are known to those of skill in the art.

As shown in the examples that follow, the capacity of the MNPs to load a compound of interest continuously increased as the amount of pluronic polymer used for MNP coating increased. Thus, any suitable amount of pluronic polymer can be used that can result in MNPs, and clusters thereof, of a size suitable for an intended use, such as the preferred MNP/MNP clusters disclosed above. In various embodiments, the MNPs comprise a molar ratio of between about 1:40 to 1:300 cyclodextrin:metal ion in the core MNP. In various further embodiments, the MNPs comprise a molar ratio of between about 1:40 to 1:250; 1:40 to 1:200; 1:40 to 1:150; 1:40 to 1:100; 1:40 to 1:80; 1:80 to 1:300; 1:100 to 1:300; 1:150 to 1:300; 1:200 to 1:300; or 1:250 to 1:300 cyclodextrin:metal ion in the core MNP. In a further embodiment, the MNPs comprise a molar ratio of between about 1:1 and 1:10 cyclodextrin:pluronic polymer; in various further embodiments, the molar ratio is between about 1:2-1:9; 1:3-1:8; 1:4-1:7; 1:5-1:6; or is about 1:1, 1:2, 1:3, 1:4, 1:5, 1:6, 1:7, 1:8, 1:9, or 1:10.

In another embodiment that can be combined with any of the above embodiments, the nanoparticle further comprises a therapeutic loaded into or onto the nanoparticle. As discussed herein, the MNPs of the present invention can form inclusion complexes with compounds of interest, which can penetrate body tissues and controllably release of the active compounds. Thus, the MNPs are particularly suitable as drug delivery agents. Any suitable technique for loading one or more compounds into the MNPS of the invention can be used, including but not limited to those disclosed below. Any suitable therapeutic can be loaded into (ie: within the MNP structure) or onto (ie: on the MNP surface), including but not limited to analgesics, anti-inflammatory agents, anthelmintics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, beta-blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leucotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof.

Specific, non-limiting examples of suitable drugs include acutretin, albendazole, albuterol, aminogluthemide, amiodarone, amlodipine, amphetamine, amphotericin B, atorvastatin, atovaquone, azithromycin, baclofen, beclomethsone, benezepril, benzonatate, betamethasone, bicalutanide, budesonide, bupropion, busulphan, butenafine, calcifediol, calciprotiene, calcitriol, camptothecan, candesartan, capsaicin, carbamezepine, carotenes, celecoxib, cerivistatin, cetrizine, chlorpheniramine, cholecalciferol, cilostazol, cimetidine, cinnarizine, ciprofloxacin, cisapride, clarithromycin, clemastine, clomiphene, clomipramine, clopidrogel, codeine, coenzyme Q10, curcumin, cyclobenzaprine, cyclosporine, danazol, dantrolene, dexchlorpheniramine, diclofenac, dicoumarol, digoxin, dihydro epiandrosterone, dihydroergotamine, dihydrotachysterol, dirithromycin, donepezil, efavirenz, eposartan, ergocalciferol, ergotamine, essential fatty acid sources, etodolac, etoposide, famotidine, fenofibrate, fentanyl, fexofenadine, finasteride, flucanazole, flurbiprofen, fluvastatin, fosphenylion, frovatriptan, furazolidone, gabapentin, gemfibrozil, glibenclamide, glipizide, glyburide, glymepride, griseofulvin, halofantrine, ibuprofen, irbesartan, irinotecan, isosorbide dinitrate isotreinoin, itraconazole, ivermectin, ketoconazole, ketorolac, lamotrigine, lanosprazole, leflunomide, lisinopril, loperamide, loratadine, lovastatin, L-thryroxine, lutein, lycopene, medroxyprogesterone, mefepristone, mefloquine, megesterol acetate, methadone, methoxsalen, metronidazole, metronidazole, miconazole, midazolam, miglitol, minoxidil, mitoxantrone, montelukast, nabumetone, nalbuphine, naratiptan, nelfinavir, nifedipine, nilsolidipine, nilutanide, nitrofurantoin, nizatidine, omeprazole, oprevelkin, osteradiol, oxaprozin, paclitaxel, paricalcitol, paroxetine, pentazocine, pioglitazone, pizofetin, pravastatin, prednisolone, probucol, progesterone, pseudo-ephedrine, pyridostigmine, rabeprazole, raloxifene, refocoxib, repaglinide, rifabutine, rifapentine, rimexolone, ritanovir, rizatriptan, rosigiltazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terzosin, tetrahydrocannabinol, tiagabine, ticlidopine, tirofibran, tizanidine, topiramate, topotecan, toremifene, tramadol, tretinoin, troglitazone, trovafloxacin, ubidecarenone, valsartan, venlafaxine, vertoporfin, vigabatrin, vitamin A, vitamin D, vitamin E, vitamin K, zafirlukast, zileuton, zolmitriptan, zolpidem, and zopiclone. Of course, salts, isomers and derivatives of the above-listed hydrophobic active ingredients may also be used, as well as mixtures thereof.

Illustrative anticancer drugs include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene hcl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, curcumin, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflomithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/ macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxol, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof.

The therapeutic-loaded MNPs can be separated from the free drug using any suitable technique, including but not limited to magnetic separation or centrifugation. The therapeutic-loaded MNPs can washed as desired by re-suspending them in water and then separated by, for example, magnetic separation or centrifugation. Further, the drug-loaded MNPs can be dispersed in an appropriate volume of sterile buffer and stored under any suitable condition (ex: refrigerated; frozen, etc.) until further use.

In another embodiment that can be combined with any of the above embodiments, the MNP further comprises a cell-targeting compound bound to the nanoparticle. In this embodiment, the MNP can be conjugated to a compound suitable to provide for targeting of the MNP to a cell or tissue of interest. Any suitable cell-targeting compound can be used, including but not limited to antibodies or fragments thereof that target the MNP to a specific tissue. Such cell-targeting compounds are known to those of skill in the art. Any suitable linkage of the cell-targeting compound to the MNP can be used.

In another embodiment that can be combined with any of the above embodiments, the MNP further comprises a photosensitizer, for use of the MNPs in photodynamic therapy, as described herein. Any suitable photosensitizer can be used, including but not limited to porphyrins, chlorophylls, dyes, aminolevulinic acid (ALA), silicon phthalocyanine Pc 4, m-tetrahydroxyphenylchlorine (mTHPC), mono-L-aspartyl chlorine (Npe6). A variety of photosensitizers are commercially available for clinical use, such as ALLUMERA™, PHOTOFRIN™ (porfimer sodium), VISUDYNE™ (benzoporphyrin derivative) LEVULAN™ (ALA), FOSCAN™ (temoporfin, a porphyrin derivative), METVIX™ (methyl aminolevulinate), HEXVIX®, CYSVIEW™, and LASERPHYRIN™ (Npe6).

The MNPs may be present in a suitable formulation for an intended delivery route. In non-limiting embodiments, the formulation is selected from the group consisting of tablets, gelcaps, softgels, and capsules. The formulations may be made up in a solid form (including granules, powders or suppositories) or in a liquid form (e.g., emulsions). The formulations of the invention may be applied in a variety of solutions and may be subjected to conventional pharmaceutical operations such as sterilization and/or may contain conventional adjuvants, such as preservatives, stabilizers, wetting agents, emulsifiers, buffers etc.

Formulations intended for oral use may be prepared according to any method known to the art for the manufacture of pharmaceutical compositions and such compositions may contain one or more agents selected from the group consisting of sweetening agents, flavoring agents, coloring agents and preservative agents in order to provide palatable preparations. Tablets contain the formulations in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the MNPs are mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

In a second aspect, the present invention provides methods for making magnetic nanoparticles, comprising
 (a) precipitation of metal salts in the presence of ammonia to obtain metal oxide core nanoparticles; and
 (b) coating the metal oxide core nanoparticles with:
  (i) cyclodextrin; and
  (ii) a pluronic polymer.

Figure 12:
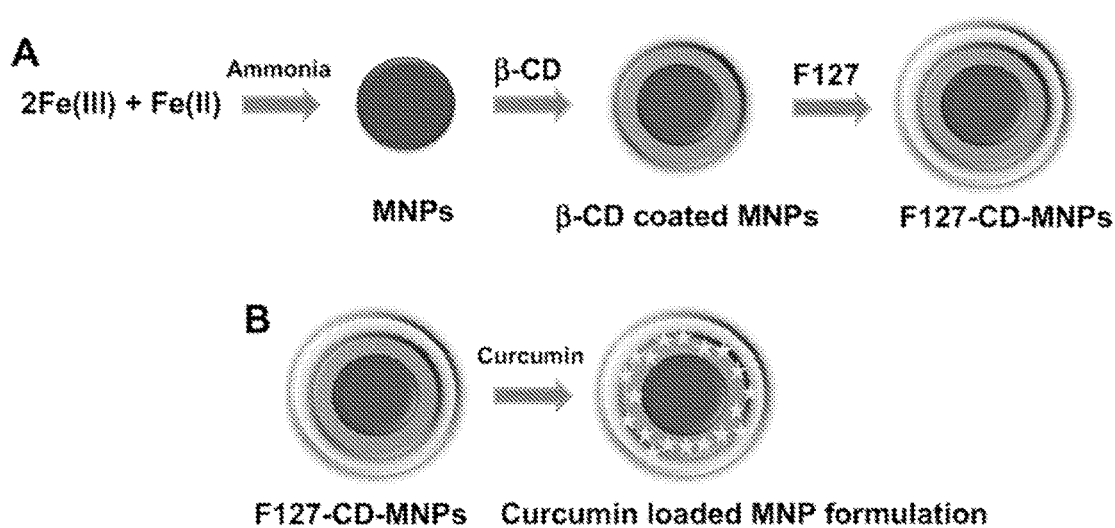
FIG. 12. Synthesis route of multi-layer coated magnetic nanoparticle (MNP) formulation and curcumin drug loading process. (A) Iron salt precipitation into iron oxide (magnetic) nanoparticles and β-cyclodextrin and F127 polymer coatings leads to F127-CD-MNP (F127250) nanoformulation. (B) Curcumin (200 µl of curcumin in acetone, 10 mg/ml) loading into F127250 magnetic nanoparticles (10 mg of particles in 3 ml 1×PBS buffer) is carried out via diffusion process. Loading is estimated using UV-vis spectrophotometer.

The present invention provides a precipitation approach to produce MNPs with multi-functional properties, as described above. A general outline of the synthetic scheme is shown in FIG. 12.

Any suitable metal salts can be used, including but not limited to iron, nickel and/or cobalt-based salts. In one preferred embodiment, iron salts are used, such as $Fe^{3+}$ and/or $Fe^{2+}$; when used in combination, it is further preferred that the molar ratio be between about 3:1 and 1:1 $Fe^{3+}$ to $Fe^{2+}$ ions; more preferably about 2:1 $Fe^{3+}$ and/or $Fe^{2+}$ ions. Suitable iron salts include, but are not limited to, iron(II) sulfate, iron(II) nitrate, iron(II) chloride, iron(II) perchlorate, iron(III) sulfate, iron(III) nitrate, iron(III) chloride, iron(III) perchlorate, and mixtures thereof.

Any suitable cyclodextrin can be used. In various preferred embodiments, the cyclodextrins are selected from the group consisting of α-cyclodextrin (six membered sugar ring molecule), β-cyclodextrin (seven sugar ring molecule), and γ-cyclodextrin (eight sugar ring molecule), and derivatives thereof. In a further preferred embodiment, the cyclodextrin comprises β-cyclodextrin, or derivatives thereof. Cyclodextrins are commercially available and can be made by means known in the art. Any suitable means for forming a layer of cyclodextrin on the MNP can be used, including but not limited to those disclosed below.

As shown in the examples that follow, the capacity of the MNPs to load a compound of interest continuously increased as the amount of cyclodextrin used for MNP coating increased. Thus, any suitable amount of cyclodextrin can be used that can result in MNPs, and clusters thereof, of a size suitable for an intended use, such as the preferred MNP/MNP clusters disclosed above. In various embodiments, the MNPs comprise a molar ratio of between about 1:40 to 1:300 cyclodextrin:metal ion in the core MNP. In various further embodiments, the MNPs comprise a molar ratio of between about 1:40 to 1:250; 1:40 to 1:200; 1:40 to 1:150; 1:40 to 1:100; 1:40 to 1:80; 1:80 to 1:300; 1:100 to 1:300; 1:150 to 1:300; 1:200 to 1:300; or 1:250 to 1:300 cyclodextrin:metal ion in the core MNP.

Pluronic polymers ("poloxamers") suitable for use in the methods of this aspect of the invention are as discussed above. In one preferred embodiment, the pluronic polymer comprises an ethylene oxide/propylene oxide block copolymer. Pluronic polymers are commercially available, and methods for their synthesis are known to those of skill in the art.

As shown in the examples that follow, the capacity of the MNPs to load a compound of interest continuously increased as the amount of pluronic polymer used for MNP coating increased. Thus, any suitable amount of pluronic polymer can be used that can result in MNPs, and clusters thereof, of a size suitable for an intended use, such as the preferred MNP/MNP clusters disclosed above. In various embodiments, the MNPs comprise a molar ratio of between about 1:40 to 1:300 cyclodextrin:metal ion in the core MNP. In various further embodiments, the MNPs comprise a molar ratio of between about 1:40 to 1:250; 1:40 to 1:200; 1:40 to 1:150; 1:40 to 1:100; 1:40 to 1:80; 1:80 to 1:300; 1:100 to 1:300; 1:150 to 1:300; 1:200 to 1:300; or 1:250 to 1:300 cyclodextrin:metal ion in the core MNP. In a further embodiment, the MNPs comprise a molar ratio of between about 1:1 and 1:10 cyclodextrin:pluronic polymer; in various further embodiments, the molar ratio is between about 1:2-1:9; 1:3-1:8; 1:4-1:7; 1:5-1:6; or is about 1:1, 1:2, 1:3, 1:4, 1:5, 1:6, 1:7, 1:8, 1:9, or 1:10.

In another preferred embodiment, the reaction is carried out in the presence of a nitrogen atmosphere to prevent oxidation. In a further embodiment, the reaction is carried out with agitation, such as stirring. Any suitable stirring speed can be used as appropriate for a desired synthetic procedure. In one embodiment, the stirring speed is between about 200 rpm and 1000 rpm, overnight.

In one exemplary embodiment, a synthetic scheme is carried out as follows: Pure magnetic nanoparticles are prepared by co-precipitation from a solution comprising $Fe^{2+}/Fe^{3+}$ ions and cyclodextrin (in a desired amount) under nitrogen atmosphere with stirring. To this solution, ammonium hydroxide is added and the stirring speed increased to uniformly precipitate MNPs. After a suitable amount of time, a suitable amount of pluronic polymer is added to the MNP suspension while stirring to achieve a thin coating. The resulting precipitate is stirred overnight to evaporate excess ammonia, washed, resuspended in water, and centrifuged to remove larger aggregates.

In a further embodiment, the methods comprise loading a therapeutic or photosensitizer into the MNP. Any suitable therapeutic or photosensitizer can be used; examples are as described above. In a preferred embodiment, the therapeutic of photosensitizer is hydrophobic. Any suitable technique for such loading can be used, including but not limited to those disclosed herein. In one non-limiting exemplary embodiment, a desired amount of therapeutic is suspended in an appropriate solvent, such as water, an alcohol (e.g., methanol, ethanol, or isopropanol), acetone, or DMSO, and added drop-wise to an aqueous dispersion of MNPs of the invention while stirring on a magnetic plate. The mixture can be stirred for any suitable period of time to permit the therapeutic to penetrate the cyclodextrin and/or pluronic polymer layers surrounding the MNP core.

The therapeutic-loaded MNPs can be separated from the free drug using magnetic separation. The therapeutic-loaded MNPs can washed as desired by re-suspending them in water and then separated with the help of magnets. Further, the drug-loaded MNPs can be dispersed in an appropriate volume of sterile buffer and stored until further use.

In a third aspect, the present invention provides methods for one or more of drug delivery, in vivo imaging, hyperthermia applications, MRI visible targeting, photodynamic therapy, or chemotherapy, comprising administering to an individual in need thereof a magnetic nanoparticle of a relevant embodiment of the invention.

In one embodiment, the invention provides methods for drug delivery, comprising administering an MNP formulation of any embodiment of the invention, or combination of embodiments, wherein a drug is loaded into the MNPs in the formulation, to a subject in need thereof. As shown herein, the MNPs (a) exhibit lower protein binding characteristics compared to other MNP formulations (which will result in a greater circulation time); (b) are phagocytosed at a lower rate compared to other MNPs (which will also result in a greater circulation time); and (c) are taken up by a variety of cell types. Thus the MNPs are excellent drug delivery vehicles, and can be used with a wide variety of therapeutics.

Any suitable therapeutic can be loaded into (ie: within the nanoparticle structure) or onto (ie: on the surface), including but not limited to analgesics, anti-inflammatory agents, anthelmintics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, beta-blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leucotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof.

In all of these embodiments, the methods comprise administering an amount effective of the therapeutic to treat the relevant disorder in the subject. The MNPs can be concentrated at a site of interest in the subject by using an externally applied magnetic field, as will be understood by those of skill in the art based on the teachings herein.

Specific, non-limiting examples of suitable drugs include acutretin, albendazole, albuterol, aminogluthemide, amiodarone, amlodipine, amphetamine, amphotericin B, atorvastatin, atovaquone, azithromycin, baclofen, beclomethsone, benezepril, benzonatate, betamethasone, bicalutanide, budesonide, bupropion, busulphan, butenafine, calcifediol, calciprotiene, calcitriol, camptothecan, candesartan, capsaicin, carbamezepine, carotenes, celecoxib, cerivistatin, cetrizine, chlorpheniramine, cholecalciferol, cilostazol, cimetidine, cinnarizine, ciprofloxacin, cisapride, clarithromycin, clemastine, clomiphene, clomipramine, clopidrogel, codeine, coenzyme Q10, curcumin, cyclobenzaprine, cyclosporine, danazol, dantrolene, dexchlopheniramine, diclofenac, dicoumarol, digoxin, dihydro epiandrosterone, dihydroergotamine, dihydrotachysterol, dirithromycin, donepezil, efavirenz, eposartan, ergocalciferol, ergotamine, essential fatty acid sources, etodolac, etoposide, famotidine, fenofibrate, fentanyl, fexofenadine, finasteride, flucanazole, flurbiprofen, fluvastatin, fosphenylion, frovatriptan, furazolidone, gabapentin, gemfibrozil, glibenclamide, glipizide, glyburide, glymepride, griseofulvin, halofantrine, ibuprofen, irbesartan, irinotecan, isosorbide dinitrate isotreinoin, itraconazole, ivermectin, ketoconazole, ketorolac, lamotrigine, lanosprazole, leflunomide, lisinopril, loperamide, loratadine, lovastatin, L-thryroxine, lutein, lycopene, medroxyprogesterone, mefepristone, mefloquine, megesterol acetate, methadone, methoxsalen, metronidazole, metronidazole, miconazole, midazolam, miglitol, minoxidil, mitoxantrone, montelukast, nabumetone, nalbuphine, naratiptan, nelfinavir, nifedipine, nilsolidipine, nilutanide, nitrofurantoin, nizatidine, omeprazole, oprevelkin, osteradiol, oxaprozin, paclitaxel, paricalcitol, paroxetine, pentazocine, pioglitazone, pizofetin, pravastatin, prednisolone, probucol, progesterone, pseudo-ephedrine, pyridostigmine, rabeprazole, raloxifene, refocoxib, repaglinide, rifabutine, rifapentine, rimexolone, ritanovir, rizatriptan, rosigiltazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terzosin, tetrahydrocannabinol, tiagabine, ticlidopine, tirofibran, tizanidine, topiramate, topotecan, toremifene, tramadol, tretinoin, troglitazone, trovafloxacin, ubidecarenone, valsartan, venlafaxine, vertoporfin, vigabatrin, vitamin A, vitamin D, vitamin E, vitamin K, zafirlukast, zileuton, zolmitriptan, zolpidem, and zopiclone, salts, isomers, amides, prodrugs, and derivatives thereof, as well as mixtures thereof.

In a preferred embodiment, the drugs are anticancer drugs, such as chemotherapeutics, and the methods comprise administering an amount effective of the MNPs to treat the tumor in the subject. Exemplary anticancer drugs include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene hcl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, curcumin, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflomithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxol, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, and zorubicin, or salts, isomers, amides, prodrugs, and derivatives thereof, as well as mixtures thereof.

As shown herein, the MNPs of the invention are taken up by a variety of tumor cells. Thus, the tumor may be any type, including but not limited to melanoma, breast cancer, ovarian cancer, small cell lung cancer, colon cancer, rectal cancer, testicular cancer, prostate cancer, pancreatic cancer, gastric, brain, head and neck, oral, renal cell carcinoma, hepatocellular carcinoma, non-small cell lung cancer, retinoblastoma and other tumors of the eye, endometrial cancer, cervical cancer, tubal cancer. In preferred embodiments, the tumor is an ovarian tumor, a prostate tumor, or a breast tumor. In a preferred embodiment that can be combined with any other embodiment or combination of embodiments, the anti-cancer therapeutic is curcumin, or salts, isomers, amides, prodrugs, and derivatives thereof, as well as mixtures thereof.

In another embodiment, the invention provides methods for hyperthermic treatment, comprising (a) administering an MNP formulation of any embodiment of the invention, or combination of embodiments to a subject in need of treatment so as to localize the MNPs to the vicinity of the tissue in need of hyperthermic treatment, and (b) applying an alternating magnetic field to produce heat from the MNPs in the formulation;

wherein the heat produced from the MNPs damages cells in the tissue and/or sensitizes cells in the tissue to subsequent therapy.

As shown herein, the MNPs in the formulation possess superparamagnetic characteristics and are thus useful in hyperthermic treatment methods. Such treatments are useful for treating any localized disease, including but not limited to arthritis and cancer. In this embodiment, it is preferred to use embodiments of the MNP formulations comprising increased concentrations of the pluronic polymer. As demonstrated herein, the MNP formulations exhibited a continuous increase in temperature increasing concentrations of pluronic polymer in the MNPs. As appropriate, the MNPs can be concentrated at a tissue or site of interest in the subject prior to applying the alternating magnetic field by using an externally applied magnetic field, as will be understood by those of skill in the art based on the teachings herein In a preferred embodiment, the tissue of interest is a tumor. Hyperthermic tumor treatments require locally raising the temperature in the vicinity of the tumor. In a further embodiment, the method further comprises administering chemotherapy and/or radiation therapy to the patient, to take advantage of the sensitization of the tumor cells to chemotherapy and/or radiation therapy.

In another embodiment, the invention provides methods for photodynamic treatment (PDT), comprising (a) administering an MNP formulation of any embodiment of the invention, or combination of embodiments, to a subject in need of PDT, wherein the MNPs comprise a photosensitizer; and (b) applying a light source to excite the MNP photosensitizer;

wherein the excitation of the photosensitizer produces reactive oxygen species that damage cells in the relevant tissue.

These methods can be used to treat any disorder that may benefit from PDT, including but not limited to acne, psoriasis, and tumors. To achieve selective destruction of the target area while limiting damage to normal tissues, either the MNP-photosensitizer can be applied locally to the target area, or photosensitive targets can be locally excited with light. For instance, in the treatment of skin conditions, including acne, psoriasis, and also skin cancers, the photosensitizer can be applied topically and locally excited by a light source. In the local treatment of internal tissues and cancers, after photosensitizers have been administered intravenously, light can be delivered to the target area using any suitable light source, including but not limited to endoscopes and fiber optic catheters.

Any suitable photosensitizer can be used, including but not limited to porphyrins, chlorophylls, dyes, aminolevulinic acid (ALA), silicon phthalocyanine Pc 4, m-tetrahydroxyphenylchlorine (mTHPC), mono-L-aspartyl chlorine (Npe6). A variety of photosensitizers are commercially available for clinical use, such as ALLUMERA™, PHOTOFRIN™ (porfimer sodium), VISUDYNE™ (benzoporphyrin derivative) LEVULAN™ (ALA), FOSCAN™ (temoporfin, a porphyrin derivative), METVIX™ (methyl aminolevulinate), HEXVIX®, CYSVIEW™, and LASERPHYRIN™ (Npe6).

In one non-limiting embodiment, an MNP-photosensitizer is applied as appropriate for a given subject/disorder. A waiting period of a few hours is allowed to elapse, during which time the photosensitizer is taken up by the relevant cells and, if the photosensitizer is a prodrug, the prodrug is converted to the active photosensitizer. The light source is then applied (such as from a light-emitting diode array or a diode laser) on the area to be treated. The light exposure lasts a few minutes to tens of minutes, during which the photosensitizer absorbs light, exciting it to produce reactive oxygen species that react with biomolecules in the area of treatment, damaging/killing cells.

In PDT therapy, the MNPs can be concentrated at a site of interest in the subject by using an externally applied magnetic field, although this is not required since the light source can be applied to a limited area, thus limiting the area of cell damage.

In all therapeutic embodiments of the invention, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

The subject can be any suitable subject that can benefit from the therapeutic or diagnostic treatment. In one embodiment, the subject is a mammal, such as a human.

As used herein, "treat" or "treating" means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

Amounts effective for these uses depend on factors including, but not limited to, the nature of the compound (specific activity, etc.), the route of administration, the stage and severity of the disorder, the weight and general state of health of the subject, and the judgment of the prescribing physician. It will be understood that the amount of the MNP formulation-therapeutic thereof actually administered will be determined by a physician, in the light of the above relevant circumstances. In one non-limiting embodiment, an amount effective is an amount that provides between 10 mg and 10 g of drug per day.

In another embodiment, methods for in vivo imaging comprise (a) administering an MNP formulation of any embodiment of the invention, or combination of embodiments, to a subject in need of magnetic resonance imaging; and (b) conducting magnetic resonance imaging (MRI) on the subject;

wherein the MRI permits in vivo imaging of the relevant tissue.

In one preferred embodiment, the relevant tissue is a tumor. As shown herein, the inventors have demonstrated that the concentration of the MNPs of the invention in a tissue, such as a tumor tissue, increases MRI signal and shorter transverse relaxation times, thereby providing value for MRI applications. Furthermore, the methods of this embodiment provide for combined diagnostic and therapeutic techniques, when therapeutic-loaded MNPs are used. Suitable therapeutics/methods are as disclosed above.

In some embodiments, an external magnet can be applied prior to MRI, to localize the MNPs to a tissue of interest. In other embodiments, the methods do not include localization via an external magnet. For example, localization to tumors is generally not required, since tumors tend to disproportionately take up administered MNPs.

The MNPs can be administered via any suitable route. In preferred embodiments, the MNPs are injected intravenously or intraperitoneally. These embodiments are particularly preferred for applications involving tumor imaging.

The methods can be used in conjunction with any type of MRI scan, including but not limited to T1-weighted MRI, T2-weighted MRI, T*2-weighted MRI, spin density weighted MRI, diffusion MRI, magentization transfer MRI, $T1_{rho}$ MRI, real-time MRI, and interventional MRI.

In all of the embodiments of the methods of the invention, the MNPs may be administered orally, parenterally, topically, by inhalation or spray or rectally (depending on tissue of interest) in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of the invention and a pharmaceutically acceptable carrier. The formulations may be in a form suitable for oral use, for example, as tablets, troches, lozenges, aqueous or oily suspensions, dispersible powders or granules, emulsion, hard or soft capsules, or syrups or elixirs.

EXAMPLES

Abstract

We have developed a multi-layer approach for the synthesis of water-dispersible superparamagnetic iron oxide nanoparticles for hyperthermia, magnetic resonance imaging (MRI) and drug delivery applications. In this approach, iron oxide core nanoparticles were obtained by precipitation of iron salts in the presence of ammonia and provided β-cyclodextrin and pluronic polymer (F127) coatings. This formulation (F127250) was highly water dispersible which allowed encapsulation of the anti-cancer drug(s) in β-cyclodextrin and pluronic polymer for sustained drug release. The F127250 formulation exhibited superior hyperthermia effects over time under alternating magnetic field compared to pure magnetic nanoparticles (MNP) and 3-cyclodextrin coated nanoparticles (CD200). Additionally, the improved MRI characteristics were also observed for the F127250 formulation in agar gel and in cisplatin resistant ovarian cancer cells (A12780CP) compared to MNP and CD200 formulations. Furthermore, the drug loaded formulation of F127250 exhibited many folds of imaging contrast properties. Due to the internalization capacity of the F127250 formulation, its curcumin loaded formulation (F127250-CUR) exhibited almost equivalent inhibition effects on A2780CP (ovarian), MDA-MB-231 (breast), and PC3 (prostate) cancer cells even though curcumin release was only 40%. The improved therapeutic effects were verified by examining molecular effects using Western blotting and transmission electron microscopic (TEM) studies. F127250-CUR also exhibited haemo-compatibility, suggesting a novel nanochemo-therapuetic agent for cancer therapy.

1. INTRODUCTION

Our goal is to develop MNPs with multi-functional characteristics for drug delivery, MRI, and hyperthermia applications. These applications are complimentary to each other and provide the unique ability to review the drug delivery efficiency at the tumor site. The MNPs loaded with anti-cancer drugs with detection capabilities promotes the clinical importance of this approach. Accordingly, we have developed a formula of magnetic nanoparticles composed of iron oxide core that is subsequently coated with β-cyclodextrin (CD) and pluronic polymer (F-127). The advantages of our formulation include smaller particle size, relatively lower protein binding, higher drug loading efficacy and enhanced particles uptake in cancer cells without hampering inherent magnetization characteristics. In this investigation, we have formulated these magnetic nanoparticles which are optimized and characterized for physico-chemical properties. The magnetic and nuclear magnetic resonance (NMR) relaxometry properties were studied in detail. In addition, the nanoparticles loaded with curcumin demonstrated an enhanced uptake in cancer cells and exhibited improved therapeutic effect of curcumin in in vitro cell culture models.

2. MATERIALS AND METHODS 2.1. Materials

Fe(III) chloride hexahydrate (99%), Fe(II) chloride tetrahydrate (99%), ammonium hydroxide (28% w/v in water), β-cyclodextrin (CD), pluronic polymer (F127), curcumin (≥95% purity, (E,E)-1,7-bis(4-Hydroxy-3-methoxyphenyl)-1,6-heptadiene-3,5-dione), acetone (≥99.5, ACS reagent grade), dimethyl sulphoxide (DMSO) (anhydrous grade), ammonium acetate, hydroxylamine hydrochloride (reagent grade, 99%), 1,10-phenontroline (99%), ammonium iron (II) persulphate hexahydrate (99%), bovine serum albumin (BSA) (96%) and hydrochloric acid (HCl) (34-37%) were purchased from Sigma Chemical Co. (St Louis, Mo., USA). All the chemicals and reagents were used without further purification. Bacto nutrient agar dehydrated was purchased from Difco Laboratories (Detroit, Mich., USA). Millipore Milli-Q® (Burlington, Mass., USA) purified water was used to make all aqueous solutions.

2.1.1. Cell Culture

A2780CP ovarian cancer cells were generously provided by Dr. Stephen Howell (University of California, San Diego, USA). MDA-MB-231, MCF-7 breast cancer cells were generously provided by Dr. W. Keith Miskimins (Director, Cancer Biology Research Center, Sanford Research/USD, Sioux Falls, S. Dak., USA), and PC3 prostate cancer cells were generously provided by Dr. Meena Jaggi, (Associate Scientist, Cancer Biology Research Center, Sanford Research/USD, Sioux Falls, S. Dak., USA). These cells were maintained as monolayer cultures in RPMI-1640 medium (A2780CP and PC3 cells) or Dulbecco's Modified Eagle's Medium-High Glucose (DMEM-Hi) (MDA-MB-231 and MCF-7) (Hyclone Laboratories, Inc., Logan, Utah, USA) supplemented with 10% fetal bovine serum (Atlanta Biologicals, Lawrenceville, Ga., USA) and 1% penicillin-streptomycin (Gibco BRL, Grand Island, N.Y., USA) at 37° C. in a humidified atmosphere (5% $CO_2$).

2.2. Synthesis of Magnetic Nanoparticles (MNPs) Formulations 2.2.1. Pure Magnetic Nanoparticles (MNPs)

Pure magnetic nanoparticles were prepared by co-precipitating $Fe^{2+}$ and $Fe^{3+}$ ions in the presence of aqueous ammonia solution [31] under nitrogen atmosphere. About 45 ml of water containing 810 mg of $Fe^{3+}$ and 297 mg of $Fe^{2+}$ ions (molar ratio 2:1) in a 100 ml beaker was stirred at 400 rpm under nitrogen atmosphere on a stir plate for 20 min. To this solution, 3 ml of ammonium hydroxide was slowly added and the speed was increased to 900 rpm in order to uniformly precipitate magnetic nanoparticles. The resulting precipitate was stirred overnight to evaporate excess ammonia. After three washes with water, the nanoparticles were resuspended in 25 ml water and centrifuged at 1000 rpm to remove larger aggregates. The supernatant stock solution was kept refrigerated until further use.

2.2.2. β-Cyclodextrin Modified Magnetic Nanoparticles

Similar to the previous method, the surface modified magnetic nanoparticles with β-cyclodextrin (CD) were prepared using 45 ml of water containing 810 mg of $Fe^{3+}$ and 297 mg of $Fe^{2+}$ ions (molar ratio 2:1), and varying amounts of CD (50-300 μg), that was stirred at 400 rpm in a 100 ml beaker under nitrogen atmosphere on a stir plate for 20 min. To these solutions, 3 ml of ammonium hydroxide was slowly added and the speed was adjusted to 900 rpm. The resulting precipitate was stirred overnight to evaporate excess ammonia. After washing, the nanoparticles were resuspended in water and centrifuged to remove larger aggregates as described above. The stock solutions were designated as CD50, CD100, CD150, CD200, CD250 and CD300 formulations according to the amount of CD used.

2.2.3. β-Cyclodextrin-Pluronic Modified Magnetic Nanoparticles

To prepare these formulations, 45 ml of water containing 810 mg of $Fe^{3+}$ and 297 mg of $Fe^{2+}$ ions (molar ratio 2:1), and 200 mg of β-cyclodextrin, was placed in a 100 ml beaker and stirred for 20 min on a stir plate at 400 rpm under nitrogen atmosphere. To this solution, 3 ml of ammonium hydroxide was slowly added and speed was adjusted to 900 rpm. After 6 hrs, 50 mg of pluronic polymer (F127) was added to the nanoparticles suspension while stirring to achieve a thin coating. The resulting precipitate was stirred overnight to evaporate excess ammonia. After triple washes with water, the nanoparticles were resuspended in 25 ml water and centrifuged at 1000 rpm to remove larger aggregates. This formulation was designated as F12750. Similarly, various F127 coated formulations (F127100, F127150, F127200, F127250 and F127300) were also prepared using 100, 150, 200, 250, and 300 mg of F127 polymer.

2.3. Characterization of Magnetic Nanoparticle Formulations 2.3.1. Particles Size and Zeta Potential The particles size, distribution and zeta potential of magnetic nanoparticle formulations were determined using Zetasizer (Nano ZS, Malvern Instruments, Malvern, UK) based on dynamic light scattering principle technique. For these measurements, 25 μl of 1 mg/ml nanoparticles suspension was added to 3 ml of distilled water and ultra sonication was applied for 30 seconds. To determine particles size and distribution, particles suspension was measured at 3 min at 25° C. An average diameter and distribution of particles size was reported from 3 runs of each formulation. The zeta potential of nanoparticles formulations was based on the average of 3 readings (each reading=30 runs).

2.3.2. Particles Size and Morphology

Nanoparticles size and morphology were evaluated using JEOL-1210 Transmission Electron Microscope (TEM) (JEOL, Tokyo, Japan) operating at 60 kV. For these measurements, 50-100 μl of nanoparticles suspension (500 μg/ml) in water was ultra sonicated for 30 seconds and carefully placed on 200 mesh formvar-coated copper TEM grid (grid size: 97 μm) (Ted Pella, Inc., Redding, Calif., USA). The excess suspension on the grid was removed using a piece of fine filter paper and the samples were allowed to air dry for 10 hours prior to imaging the particles under the microscope.

2.3.3. Physical Characterization

For the physical characterization of Fourier transform infrared (FTIR) spectra, X-ray diffraction (XRD) and thermo-gravimetric analyzer (TGA), the magnetic nanoparticle formulations were lyophilized to obtain dry solid particles using the Labconco Freeze Dry System (−48° C., $133 \times 10^{-3}$ mBar; Labconco, Kansas City, Mo., USA). The FTIR of particles were recorded employing a Smiths Detection IlluminatIR FT-IR microscope (Danbury, Conn., USA) with diamond ATR objective. FTIR spectra of samples were acquired by placing nanoparticles on the tip of the ATR objective. Data was acquired between 4000-750 $cm^{-1}$ at a scanning speed of 4 $cm^{-1}$ for 32 scans. The average data of 32 scans was presented as FTIR spectra. X-ray diffraction (XRD) patterns of nanoparticles were recorded employing a D/Max-B Rikagu diffractometer (Rigaku Americas Corporation, Woodlands, Tex., USA) using Cu radiation at =0.1546 nm and operating at 40 kV and 40 mA. The samples were mounted on double sided silicone tape and measurements were performed at 2θ from 20 to 70°. Thermo-gravimetric analysis of nanoparticles was accomplished on a TA Instruments Q50 TGA (TA Instruments, New Castle, Del., USA) from 25° C. to 700° C. at a heating ramp of 10° C., under a constant flow (100 ml/min) of nitrogen gas.

2.4. Curcumin Loading

Curcumin (CUR) was used as a model cancer prevention and therapeutic drug. Diluted CUR in acetone (200 μl, 10 mg/ml) was added drop-wise to an aqueous dispersion of magnetic nanoparticles (10 mg of particles in 3 ml water) while stirring at 400 rpm on a magnetic plate. The mixture was stirred overnight so that the CUR molecules would penetrate the CD or CD-F127 polymer layers surrounding the nanoparticles core. The CUR loaded nanoparticles were separated from the free drug using magnetic separation [32]. The drug-loaded nanoparticles were washed three times by re-suspending them in water and then separated with the help of magnets. Finally, the drug-loaded nanoparticles were dispersed in 2 ml sterile PBS solution in a refrigerator until further use. The curcumin loading estimation was determined using UV spectrophotometer at 450 nm, following our previously reported procedure [33].

2.5. Magnetic Properties

The hysteresis for solid iron oxide formulations (2-3 mg) was measured in a small polypropylene straw with a Lakeshore vibrating sample magnetometer using maximum fields of 150 Oe. Their long axis was oriented parallel to the external field. The saturation magnetization (Ms) was determined from Ms versus plots and extrapolated to infinite fields. The heating effects of formulations (hyperthermia phenomenon) were evaluated with 1 ml of iron oxide formulations (200 μg to 5 mg of formulation/ml) at H=150 Oe and f=300 kHz. The temperature rise in the formulation was measured with a thermocouple immediately after the magnetic field was turned off. Similarly, the heating efficacy of these formulations was also evaluated with 1 ml of iron oxide formulations (200 μg to 5 mg of formulation/ml) containing 3% (w/v) agar solution phantom gels at H=150 Oe and f=300 kHz.

2.6. In Vitro Magnetic Resonance Imaging

For MRI studies, 3% (w/v) agar solution containing different amounts of magnetic nanoparticles formulations was prepared by heating agar solution at 80° C. for about 20 min and stirring thoroughly to obtain uniform solution, then allowed to cool down to room temperature. These phantom gels were employed to test the in vitro MRI properties. In vitro MRI properties were measured using a 9.4 T (400 MHz H[1]), 89 mm vertical bore MR system (Varian, Inc. Walnut Creek, Calif., USA) equipped with triple axis gradients (100 G/cm) and a 4 cm Millipede transmit/receive radiofrequency coil. $T_1$ relaxation times of the samples were measured using a spectroscopic inversion-recovery sequence. The sequence was applied using 12 inversion times and a repetition time (TR) of 10 s [34]. $T_2$ relaxation time was measured using a spin-echo NMR spectra analysis sequence with 32 echo times arrayed exponentially from 5 to 300 ms and TR of 8000 ms. The $T_1$ and $T_2$ relaxation times were computed using a nonlinear regression applied by the system software (VnmrJ 2.3A). For further analysis, the $T_1$ and $T_2$ relaxation curves were exported so that relaxivities could be extracted by graphing the relaxation rates ($1/T_1$ and $1/T_2$) versus concentration using Origin 6.1 software. Additionally, images of each sample were acquired using a multiple-echo multiple-slice (MEMS) sequence with the following parameters: repetition time (TR), 1000 ms; echo time (TE), 8 ms; number of echoes (NE), 8; number of excitations (NEX), 4; matrix size of 128×128; and field of view 15 mm×15 mm. The concentration of iron oxide used in each formula was assessed to be within 10-40 µg Fe/ml.

2.7. Drug Delivery 2.7.1. Protein Binding

The protein binding interaction study with nanoparticles illustrates the behavior of nanoparticles in circulation. To determine an effective formulation that can be used for drug delivery application, we performed an in vitro bovine serum albumin (BSA) interaction with magnetic nanoparticle suspensions in 1×PBS solution. For this experiment, 1 ml of BSA solution (330 µg/ml) was titrated against 1 mg/ml of magnetic nanoparticle formulations. The intensity of interaction of protein molecules and nanoparticles was determined using an intrinsic fluorescence quenching in fluorescence spectrum [35]. The extent of decrease in the intensity of fluorescence due to interaction with nanoparticles was recorded between 300-500 nm at $\lambda_{ex}$=295 nm using a Shimadzu RF-5301PC Fluorimeter (Shimadzu Scientific Instruments, Columbia, Md., USA). The Chipman and Beaven methods [35, 36] were employed [Equation (1)] to determine binding constant ($k_b$) and number of binding sites or binding stoichiometry (n).

$$(F_0-F)/(F_0-F_s)=[(MNP)/K_{diss}]^n \rightarrow \quad (1)$$

where $F_0$ and $F_s$ are relative fluorescence intensities of protein solution alone and protein solution saturated with MNPs, respectively. The relative fluorescence intensity (F) was obtained from the area under the fluorescence curve and [MNP] is the concentration of nanoparticles (mg/ml). Number of binding sites (n) was obtained from the slope of plot, log $[(F_0-F)/(F-F_s)]$ vs log [MNP]. Logarithm of dissociation constant ($K_{diss}$) equals log [MNP] at log $[(F_0-F)/(F-F_s)]=0$. Binding constant ($K_b$) is reciprocal of $K_{diss}$. Standard deviations were obtained from 3 replicates.

2.7.2. Nanoparticles Cellular Uptake

To compare the cellular uptake of magnetic nanoparticles in cancer cells (A2780CP, MDA-MB-231 and MCF-7), 5×10⁵ cells were seeded in 6-well plates in 2 ml medium. After cells were attached, media was replaced with 25-100 µg of medium containing nanoparticles. After 6 hrs, cells were washed twice with 1×PBS, trypsinized, centrifuged and collected in 2 ml media. These cell suspensions (50 µl) were injected into an Acuri C6 Flow Cytometer (Accuri Cytometer, Inc., Ann Arbor, Mich., USA) to determine the side scattering height fluorescence levels in FL1 channel [32]. Standard deviations were calculated from 3 replicates.

The uptake (internalization) pattern of nanoparticles was monitored by transmission electron microscopy (TEM) to further validate the cellular uptake capability of magnetic nanoparticles in cancer cells which was visually observed. For this experiment, aforementioned cells (1×10⁷ cells per 150 mm plate) were incubated with 1 mg of particles in 20 ml media for 6 hrs. The treated cells were centrifuged and fixed with standard formaldehyde (4%)-glutaraldehyde (1%) fixative solution followed by $OsO_4$ fixative solution. Next, cells were dehydrated in a graded series of acetone and embedded in Spurr resin. These cell-containing resin blocks were sectioned using an ultramicrotome and ultrathin sections (70-90 nm thickness) were transferred onto TEM grid (grid size: 97 µm) (Ted Pella Inc., Redding, Calif., USA). The grids were processed with uranyl acetate and lead acetate solutions to visualize cellular ultra structures.

2.7.3. Quantitative Internalization Estimation of Magnetic Nanoparticle Formulations in Macrophages and A2780CP Cancer Cells To determine whether our formulations are useful for drug delivery, we have evaluated their uptake in macrophage cells and A2780CP metastatic ovarian cancer cells. For this, 5×10⁵ macrophage (RAW 264.7) cells or A2780CP cells were seeded in 6-well plates in 2 ml medium. After cells were attached, media was replaced with 50 or 100 µg of iron containing nanoparticles in medium. After 6 hrs, cells were washed twice with 1×PBS, trypsinized/scraped and centrifuged at 1000 rpm for 5 min. Obtained cell pellet was lysed in 500 µl HCl and analyzed for iron levels in cells using 1,10-phenonthroline colorimetric method [27]. Standard deviations were calculated from 3 replicates. To further confirm this uptake phenomenon in macrophages and A2780CP cells, a transmission electron microscopy (TEM) analysis was employed as explained in the previous section.

2.7.4. In Vitro Cytotoxicity (MTT Assay)

In vitro cytotoxicity was assessed using a standard 3-(4, 5-dimethylthiazol-2-yl)-2,5-diphenyltetrazolium bromide (MTT) based colorimetric assay (CellTiter 96 $AQ_{eous}$, Promega, Madison, Wis., USA). Ovarian (A2780CP), breast (MDA-MB-231), and prostate (PC3) cancer cells were used for this experiment. Cells (5000 cells/well in 100 µl media) were cultured in RPMI-1640 or DMEM medium containing 10% FBS and 1% penicillin-streptomycin in 96-well plates and allowed to attach overnight. The media was replaced with fresh media containing different concentrations (2.5-40 µM) of CUR and CUR containing MNPs (F127250-CUR). Equivalent amounts of DMSO or F127250 MNPs without drug in PBS were used as control. These plates were incubated at 37° C. for 2 days. After day 2, the media was replaced with 100 µl fresh media and the MTT reagent (25 µl/well) was added to each well and plates were incubated for 3 hrs at 37° C. in an incubator. The color intensity was measured at 492 nm using a microplate reader (BioMate 3 UV-Vis Spectrophotometer, Thermo Electron Corporation, Hudson, N.H., USA). The anti-proliferation potential of CUR and F127250-CUR treatments was calculated as a percentage of cell growth with respect to the DMSO and F127250 formulation in PBS controls. Standard deviations were obtained from 6 replicates.

2.7.5. Colony Formation

Colony formation assay was performed to determine long-term anti-cancer potential of our formulations. For this assay, cancer cells (A2780CP, MDA-MB-231, and PC3) were seeded in 2 ml media in 6-well plates (1000 per well) and allowed 2 days to initiate the colonies. Cells were then treated with different concentrations (2-10 µM) of CUR or F127250-CUR over a period of 10 days. The plates were washed three times with 1×PBS, fixed in chilled methanol, stained with hematoxylin (Fisher Scientific, Fair Lawn, N.J., USA), washed with water and air dried. The number of colonies was counted using Multimage™ Cabinet (Alpha Innotech Corporation, San Leandro, Calif., USA) and AlphaEase Fc software. The percent colonies were calculated using the number of colonies formed in treatment divided by the number of colonies formed in DMSO or F127250 without drug in PBS. Standard deviations were obtained from 3 replicates.

2.7.6. Western Blot Analysis

The immunoblot analyses were performed to determine anti-cancer effects of our formulation at the molecular level. For these experiments, cancer cells were collected after 2 days of treatment with 10 µM and 20 µM CUR and 10 µM and 20 µM of F127250-CUR and processed for protein extraction and Western blotting using standard procedures [33, 37]. The cell lysates were separated by gel electrophoresis on polyacrylamide gels containing sodium dodecyl sulfate and then transferred to PVDF membranes. The membranes were blocked with Tris-buffered saline (TBS) containing 5% (w/v) skimmed milk. After washing thrice with Tween 20, the membranes were incubated overnight with primary antibody specific to Bcl-xL or PARP at 4° C. After washing, the membranes were incubated for 1 hr with secondary antibody (Promega, Madison Wis., USA). Protein bands were visualized using the Lumi-Light Detection Kit (Roche, Nutley, N.J., USA) and detected with a BioRad Gel Doc (BioRad, Hercules, Calif., USA).

2.8. Haemocompatibility

For this study, 8 ml healthy male human blood (Donor #53554, Registration #2577632, Biological Specialty Corp, Colmar, Pa., USA) was centrifuged at 2000 rpm for 10 min and supernatant was discarded and red blood cells (RBC) were collected. RBCs were resuspended in 8 ml RPMI1640 growth media. A total 100 µl cell suspension containing RBCs was treated with CUR containing MNP, CD200 or F127250 formulations (10-100 µg). The cells were incubated for 2 hrs at 37° C., centrifuged and supernatant was collected to determine the degree of haemolysis at $\lambda_{max}$ 570 nm using absorbance spectrophotomer. The treated RBC pellets were redispersed in PBS and a drop of these solutions was placed and spread on a glass slide and images were taken under an Olympus BX 41 phase contrast microscope (Olympus, Center Valley, Pa., USA)

2.9. Statistical Analysis.

Values were processed using Microsoft Excel 2007 software and presented as mean±standard error of the mean (S.E.M.). Statistical analyses were performed using an unpaired, two tailed student t-test. The level of significance was set at *$p<0.05$. All the graphs were plotted using Origin 6.1 software.

3. RESULTS AND DISCUSSION

Although most of the conventional methodologies to produce stable water dispersible superparamagnetic iron oxide nanoparticles provide a uniform magnetic nanoparticle formulation they often fail in achieving additional features such as (i) smaller particles size, (ii) good aqueous stability over a period of time, (iii) higher magnetization, (iv) surface functionality and antibody conjugation capability, (v) higher drug/bio-macromolecular encapsulation, and (vi) bioavailability. We have employed a simple precipitation approach to develop a magnetic nanoparticle formulation with multi-functional properties, in which iron (II) and iron (III) salts are reduced by ammonia in the presence of β-cyclodextrin (CD) and pluronic polymer [(F-127, poly (ethylene-co-propylene glycol)]. Using nitrogen atmosphere throughout the preparation to prevent oxidation resulted in formulations in the form of magnetite. The developed formulations are schematically illustrated in Scheme 1. The selection of CD for this formulation is based upon its combination of hydrophilic units (—OH) which can bind to iron oxide nanoparticle surface and the presence of a hydrophobic cavity to load anti-cancer drug(s) [28, 31, 38]. F127 consists of a hydrophobic (polypropylene, PPO) chain which can bind to the hydrophobic cavities of CD and the hydrophilic (polyethylene glycol, PEO) chain provides additional hydrophilicity and stability to overall formulation [39-42]. Therefore, this formulation is comprised of an iron oxide core with the presence of hydrophobic and hydrophilic layers.

Figure 1:
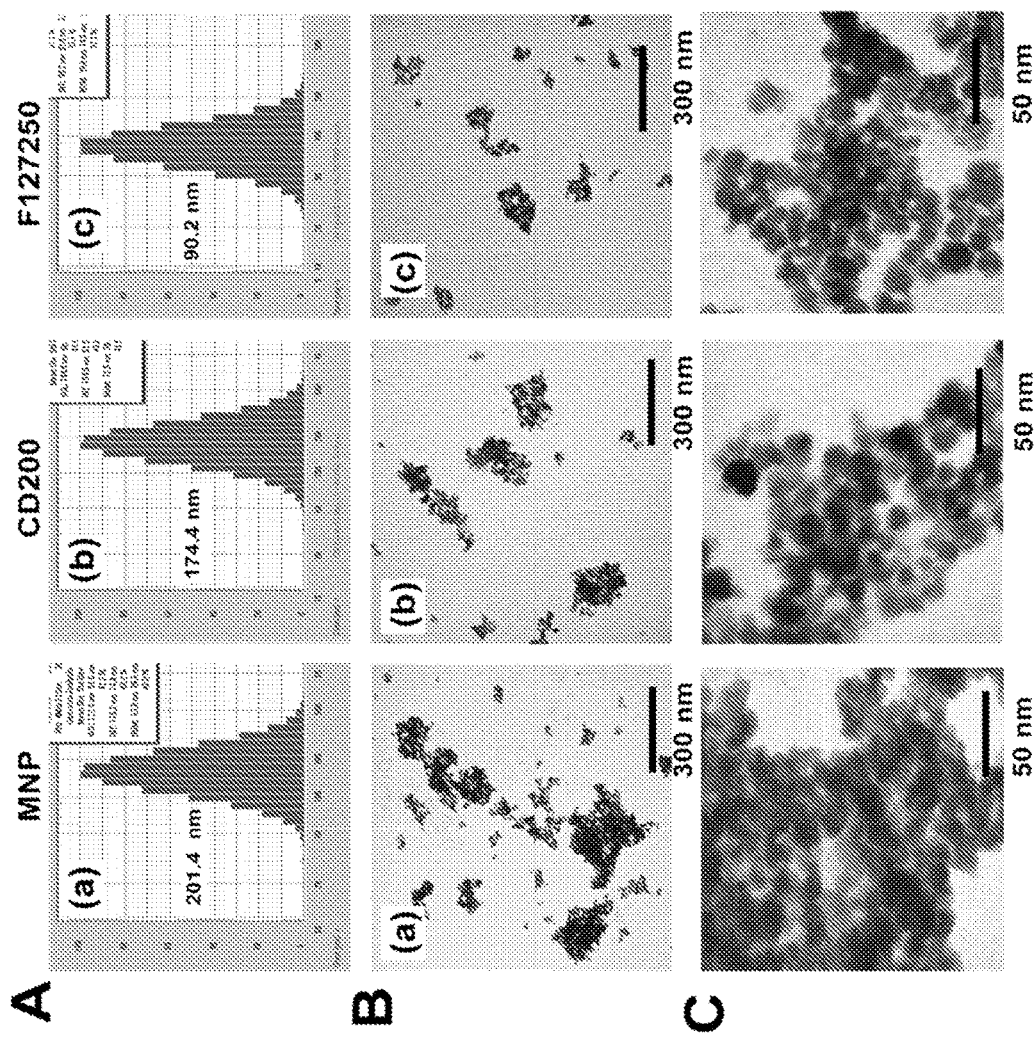
FIG. 1. Particles size characterization of magnetic nanoparticle formulations: (A) Dynamic light scattering particles size data of (a) pure magnetic nanoparticles (MNP), (b) magnetic nanoparticles coated with 200 mg of CD (CD200) and (c) magnetic nanoparticles coated with 200 mg of CD and 250 mg of F127 polymer (F127250). (B) Transmission electron microscopic images of (a) pure magnetic nanoparticles, (b) magnetic nanoparticles coated with 200 mg of CD and (c) magnetic nanoparticles coated with 200 mg of CD and 250 mg of F127 polymer. (C) Transmission electron microscopic image of (a) pure magnetic nanoparticles, (b) magnetic nanoparticles coated with 200 mg of CD and (c) magnetic nanoparticles coated with 200 mg of CD and 250 mg of F127 polymer. Data showing individual particle grain size of 7-10 nm.

3.1. Characterization of Magnetic Nanoparticles 3.1.1. Particles Size and Morphology The initial focus of our investigation was to elucidate which formulation has smaller particles size and distribution in aqueous medium after surface engineering with CD or CD and F127 polymer. The particles size and distribution measurements were obtained using a dynamic light scattering (DLS) instrument (Table 1). Pure magnetic nanoparticles (MNPs) have shown a larger particles size of 201.4 nm with a polydispersity index (PI) of 0.22%. Coating of CD (50-150 mg) onto MNPs resulted in a slight increase in particles size (208.43 nm to 256.17 nm) due to random coating and/or the formed coating layers of CD molecules on the surface were not stable. But further increases in CD (200-300 mg) for coating onto MNPs produced more uniform formulations with average particles size ~175 nm. Therefore, we have selected 200 mg of CD that is optimized to provide a good dispersion formulation. Further, it is shown that F127 polymer layer coating (50-250 mg) improves its overall stability in aqueous dispersion by reducing the size of CD200 particles from ~175 nm to ~90 nm. Overall, the DLS data suggest that CD200 and F127 coatings prevent aggregation of iron oxide formulations, unlike bare magnetic nanoparticles, conventional and multi-layer MNP formulations [4, 28, 29, 43-45] (FIG. 1A). The average cluster formation of MNPs consistently decreased with the CD and F-127 coatings. This behavior can be seen visually in TEM studies. Pure magnetic nanoparticles aggregate to have an average cluster size of >300 nm (FIG. 1B (a)). When the particles were coated with 200 mg of CD, the cluster size is decreased to 170 nm (FIG. 1B (b)). F127 polymer coating further reduced particle size and provided uniformly suspended particles with an average size of 90 nm (FIG. 1B (c)). These data suggest that CD and F127 layers on iron oxide nanoparticles not only coat particles but also attenuate their cluster behavior in aqueous media. Further, F127250 formulation particles size (90.72±0.23 nm) is considerably smaller compared to many double layered iron oxide formulations prepared by co-precipitation approach [28, 29]. However, an individual nanoparticle grain size of this formulation is slightly increased after coating with CD and F127 polymers (Table 1). But, all the individual particle grain sizes ranged between 7-10 nm which is commonly observed with many precipitation procedures [4, 14, 28, 39-42] (FIG. 1C).

Good stability in aqueous medium of CD or CD and F127 polymer coated magnetic nanoparticle formulations is due to their negative zeta potential values (Table 1). The CD coated formulations (CD50 to CD250) have −32 to +0.59 mV while CD200 with F127 coated formulations (F12750 to F127250) exhibited −9.42 to −10.79 mV. Such negative zeta potential formulations help repel each particle in the suspension, ensuring long-term stability and avoiding particles aggregation [46-48], whereas MNP formulations exhibited positive zeta potential, i.e., 6.17 mV indicates some degree of aggregation phenomenon.

3.1.2. Physical Characterization

Figure 2:
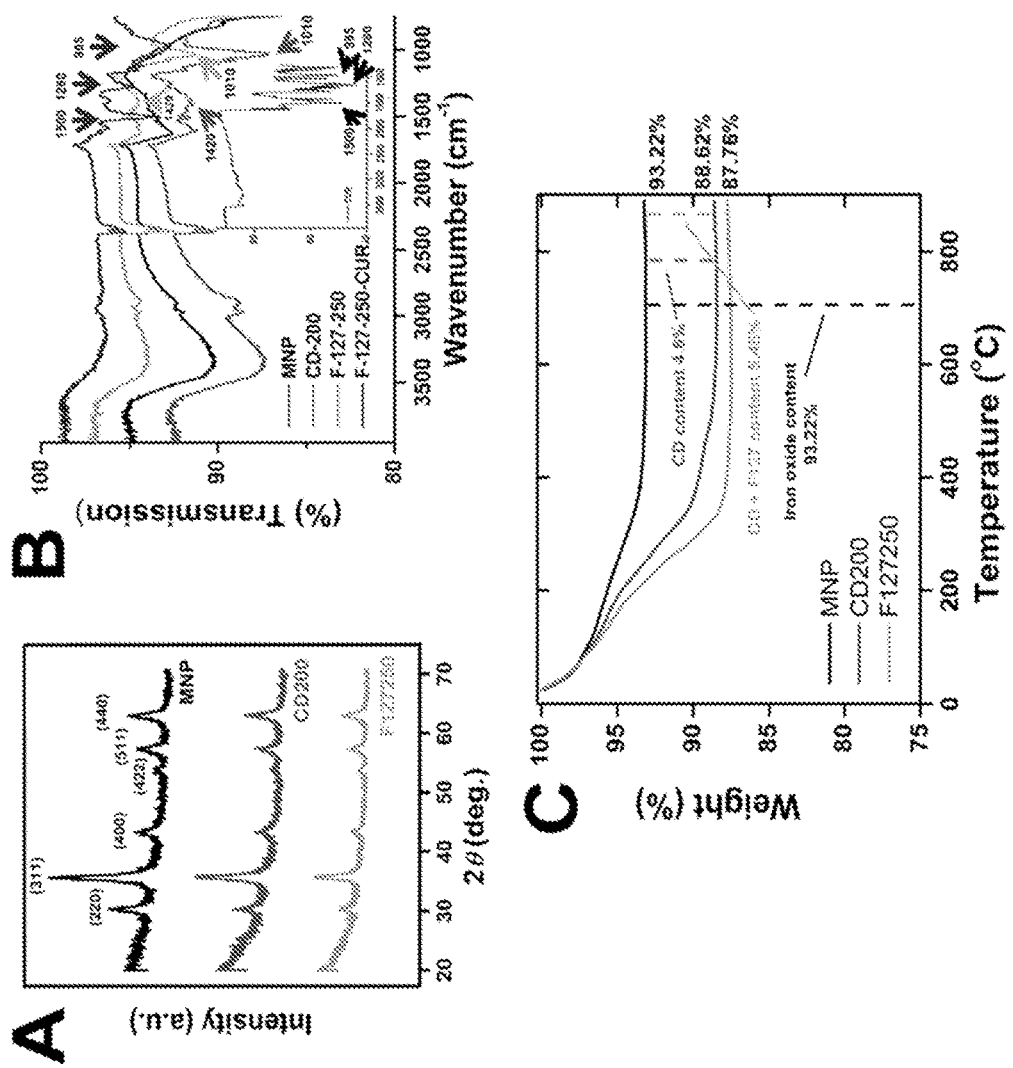
FIG. 2. Physical characterization of magnetic nanoparticle formulations: (A) X-ray diffraction patterns, (B) Fourier transform infrared spectra, and (C) thermograms of MNP, CD200, and F127250 nanoparticle formulations. Data presented is a mean of three replicates. Note: (B) also presents curcumin and curcumin containing F127250 nanoparticle formulations (F127250-CUR).

X-ray diffraction (XRD) patterns of different formulations were analyzed to determine the crystal phase of the iron oxide nanoparticles and surface engineered iron oxide nanoparticles (FIG. 2A). All the formulations (MNPs, CD200, and F127250) have shown diffraction peaks at 2θ=30.1°, 36.2°, 42.4°, 52.5°, 57.5° and 62.2° due to face centered cubic lattice structures 220, 311, 400, 422, 440 and 511 which are characteristic peaks of $Fe_3O_4$ crystal structure [31]. All of the diffraction peaks in FIG. 2A can be indexed and assigned to the cubic structure of $Fe_3O_4$ which is consistent with the theoretical values (JCPDS card no.: 01-088-0315). Additionally, there are no peaks at 31° corresponding to $\gamma-Fe_2O_3$ and $\alpha-Fe_2O_3$ for 210 and 213 in XRD patterns, supporting the purity of synthesized iron oxide nanoparticles. This clearly suggests that iron oxide formulations are composed of magnetite ($Fe_3O_4$), not maghemite. Further, formulations were stored under nitrogen atmosphere to prevent possible oxidation which is responsible for producing maghemite from magnetite.

To confirm the presence of β-cyclodextrin or F127 polymer layer(s) on magnetic nanoparticles, FTIR analysis was taken into consideration (FIG. 2B). Pure magnetic nanoparticles exhibited a broad peak between 3500-3000 $cm^{-1}$ due to the presence of hydroxyl/amino groups on the surface and a strong peak in the 550 $cm^{-1}$ region due to —O—Fe of iron oxide skeleton [32] (FIG. 2B, black line). In addition, β-cyclodextrin coated MNPs (CD200) showed an intense band at 1010 $cm^{-1}$ due to glycosidic (C—O—C) vibration and the coupled (C—C/C—O) stretch vibrations. (FIG. 2B, red line) [31]. The F127 polymer coated on the CD-MNP formulation (F127250) demonstrated the same peaks that appeared in CD200. The peak at 1010 $cm^{-1}$ belongs to the CH2 rocking and C—O—C stretch vibrations of F127 polymer (green line) [28].

We performed thermogravitic analyses to further confirm the presence of CD and F127 layer(s) on magnetic nanoparticle formulations (FIG. 2C). Pure magnetic nanoparticles have a weight loss ~6.78 wt. % (iron oxide core content 93.22 wt. %), whereas CD coated formulations lost ~11.38 wt. % (6.78 wt. % degradation of NPs+4.6 wt. % is due to CD coating) indicating 88.62 wt. % of iron oxide core in the formulation. In the case of F127250 formulations it was noticed 87.76 wt. % iron oxide core (6.78 wt. % degradation of NPs+5.46 wt. % due to CD and F127 polymer layer coatings). Thus, we can confirm that additional weight loss in the case of CD200 (4.6 wt. %) and F127250 (5.46 wt. %) formulations is due to coating of CD and F127 polymer layer(s).

3.1.3. Curcumin Loading and Release

The curcumin loading was estimated using a UV-vis spectrophotometer as described in our previous report [49]. It was confirmed that the loading capacity continuously increased as the amount of CD used for nanoparticles coating increased. This indicates that curcumin molecules were entering into the CD layer on nanoparticles via hydrophobic-hydrophobic interactions. Our recent report supports this behavior of curcumin encapsulation into the hydrophobic bucket structure of the CD molecule [38]. In addition, F127 polymer promotes its loading to a greater extent due to PPO hydrophobic chains [28]. It was also confirmed that in pure magnetic nanoparticles, curcumin is primarily on the surface of the nanoparticles. Because curcumin molecules are loosely bound to surface of nanoparticles, curcumin release is much faster, whereas CD200 and F127250 magnetic nanoparticle formulations have shown a bi-phasic release characteristic. The initial burst of release was due to immediate dissociation of surface bound curcumin molecules that exist on the CD or F127 polymer matrix. The remaining sustained drug release was due to the slow release of the drug entrapped inside CD and/or F127 polymer layers. The curcumin existence in nanoparticle layers was confirmed by FTIR analysis. Curcumin exhibited sharp absorption bands at 1605 $cm^{-1}$ (stretching vibrations of benzene ring), 1502 $cm^{-1}$ (C=O and C=C vibrations of benzene), 1435 $cm^{-1}$ (olefinic C—H bending vibration), 1285 $cm^{-1}$ (aromatic C—O stretching vibrations), and 1025 $cm^{-1}$ (C—O—C stretching vibrations of CUR) (FIG. 2B, inset, black line). The curcumin encapsulated formulation F127250-CUR also exhibited all these peaks in addition to the parent F127250 formulation (FIG. 2B, blue line), indicating the presence of curcumin in the formulation.

3.2. Hyperthermia Application

Figure 3:
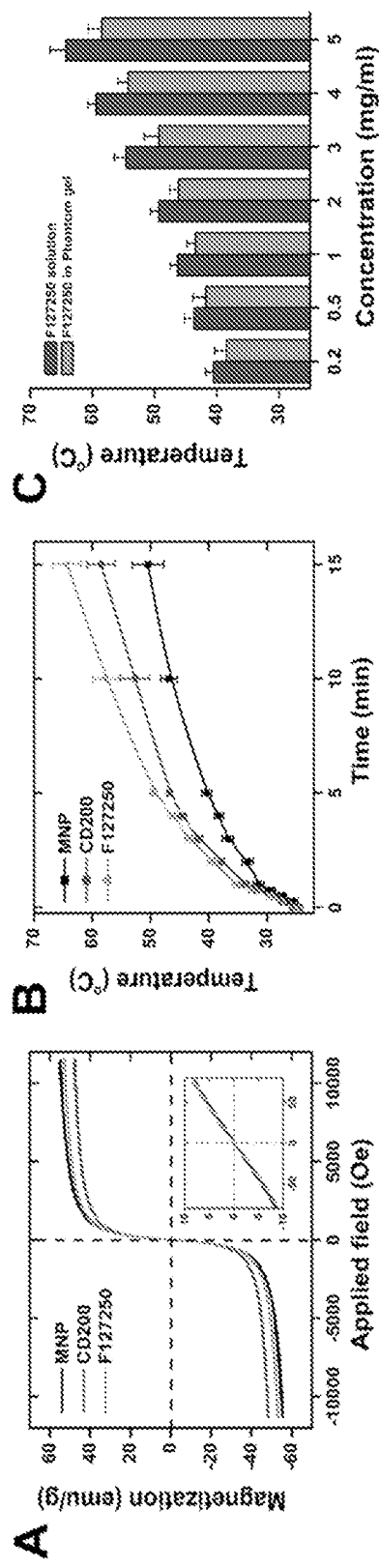
FIG. 3. (A) Hysteresis loops of MNP, CD200 and F127250 nanoparticle formulations at room temperature. (B) Time course of the raised temperature of MNP, CD200 and F127250 nanoparticle formulations under an alternating magnetic field operating at 300 kHz. (C) Temperature of various concentrations of F127250 nanoparticles in solution and agarose gels after altering magnetic field applied for 15 min.

Magnetic nanoparticles are especially susceptible to induce localized hyperthermia in an alternating magnetic field which may potentially shirk or destroy the tumors and sensitize to radiation or chemo-therapies [50-54]. Iron oxide based magnetic nanoparticle formulations are often employed for this purpose because of fewer side effects [55, 56]. For a given magnetic targeted application, an iron oxide formulation needs to meet superparamagnetic properties (high saturation magnetization, Ms) with greater heat effect. Therefore, our formulations were evaluated for magnetic properties, i.e., magnetic saturation (Ms), using a vibrating sample magnetometer at 300 K and at alternating ±12000 Oe magnetic field (FIG. 3A). The MNP, CD200 and F127250 formulations have saturation magnetization values of 54.47, 47.51 and 52.58 emu/g, respectively. These saturation magnetization values correlate with the reported values for many polymer stabilized iron oxide nanoparticle formulations [32, 34, 57]. This slight variation between the formulations is due to coating with F127 polymer and/or β-cyclodextrin, and a small variation in overall particles size. Further, no coercivity and remanence were observed for any of the formulations at lower magnetic field curves, confirming superparamagnetic characteristics (FIG. 3A, inset).

The deficiency of hyperthermic cancer treatment is due to the difficulty of raising the tissue temperature properly [58]. Hyperthermia using magnetic nanoparticles can raise the temperature in the tumor locally up to 41-45° C. and is capable of damaging the tumor cells without damaging the healthy cells [59]. Our formulations were tested for these heating effects and results are presented in FIG. 3B. The temperature of formulations is plotted as a function of time at the field of 150 Oe and a constant frequency of 300 kHz. The heating effects (hyperthermia) of formulations resulted from absorbing energy from the alternating magnetic field which was transformed into heat by means of hysteresis loss during reversal of magnetization. The order of heating effects of formulations was found to be F127250>CD200>MNP. This can be explained since iron oxide core is available for excellent heat effects in the modified formulation of F127250 due to its freely dispersed stage, in contrast to other formulations. On the other hand, smaller clustered particles have a higher specific surface area which generates higher heat [59]. Therefore, we speculate the F127250 nanoparticles formulation would be highly useful as thermoseeds for localized hyperthermia treatment of cancers. Additionally, our formulations exhibited a continuous increase in temperature with respect to an increased concentration of F127250 formulations employed (FIG. 3C). This behavior is similar whether it is in solution form or in the gel form. This is further support that the heat buildup is uniform throughout the sample.

3.3. Magnetic Resonance Imaging

Nanomedicine platforms combine therapeutic function with imaging abilities which have proven to be the next generation of medicine [41]. Unlike traditional contrast agents or drugs, image visible nanomedicine has the ability for simultaneous diagnosis and therapy in one formulation [20, 21, 23]. We have evaluated our iron oxide formulations for in vitro MRI agent characteristics. These tailor-made cocktails can address the challenges of tumor heterogeneity and adaptive resistance which can ultimately help achieve the goal of personalized medicine for cancer therapy [63].

Figure 4:
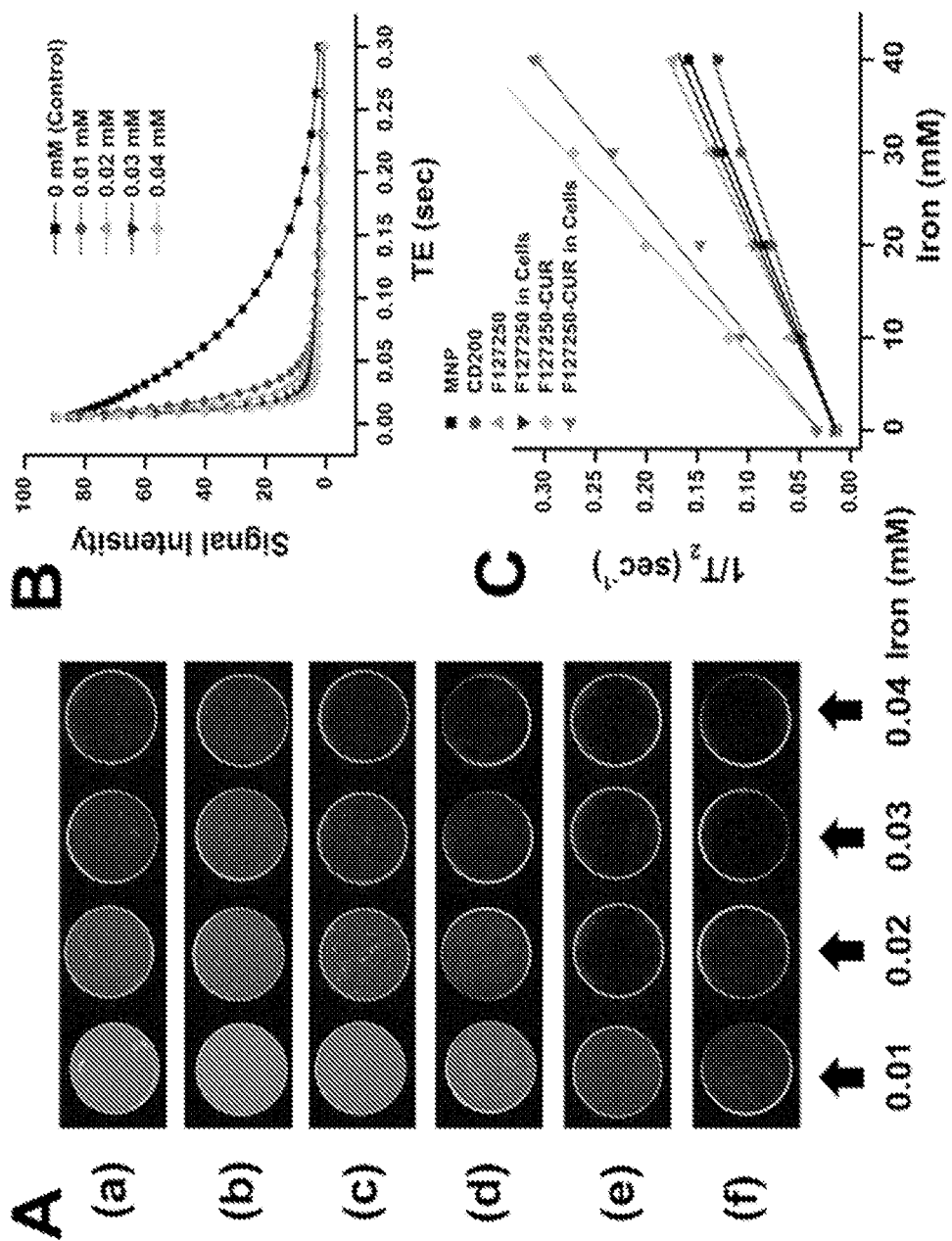
FIG. 4. Magnetic resonance image (MRI) characteristics of magnetic nanoparticle formulations: (A) Signal intensity $T_2$ weighted mR images of magnetic nanoparticle formulations in phantom agar gel at 10-40 µg/ml concentration at 25° C. (a) MNP, (b) CD200, (c) F127250, (d) F127250 in A2780CP cells, (e) F127250-CUR and (f) F127250-CUR in A2780CP cells. (B) $T_2$ relaxation curves of various magnetic nanoparticle formulations in phantom agar gel. (C) $T_2$ relaxation rates ($1/T_2$) plotted as a function of the Fe concentration for various magnetic nanoparticle formulations.

Based upon the collected images (FIG. 4A), increased concentration of MNPs resulted in a greater reduction in signal. Relative to the control gel, the increase in iron oxide concentration also resulted in shorter transverse relaxation times (FIG. 4B). For example, as the concentration of iron oxide in the MNP increased from 10 µg Fe/ml to 40 µg Fe/ml, $T_2$ relaxation times diminished from 20.8 ms to 6.3 ms. Similar to $T_2$ relaxation times, longitudinal relaxation $T_1$ noted a reduction in relaxation time with iron concentration. By plotting the transverse relaxation rate, $R_2$, ($1/T_2$) as a function of the concentration of Fe in each sample, $R_2$ increased linearly with the concentration of Fe (FIG. 4C) in all the formulations according to the equation: $R_2 = 1/T_2 = 1/T^0_2 + r_2*[Fe]$, where $1/T_2$ is the relaxation rate in the presence of iron oxide, $1/T^0_2$ is the relaxation rate of pure water, $r_2$ is the transverse relaxivity, and [Fe] is the concentration of iron in each sample. The $T_2$ relaxivity ($r_2$) was found to decrease in the following order for the tested compounds: F127250-CUR>F127250-CUR in cells>F127250>F127250 in cells>MNP>CD200. In comparison to $T_2$ relaxation, application of F127250 to curcumin with and without cells resulted in an increase in relaxivity. For example, the $r_1$ for F127250-CUR was found to be $28.6 \times 10^{-3} s^{-1} \mu g^{-1}$ ml; whereas, F127250 had a relaxivity of $12.5 s^{-1} \mu g^{-1}$ ml. The observed difference suggests that curcumin increases local inhomogeneity in the magnetic field. For $T_2$-weighted imaging procedures, the F127250 MNP can potentially improve observation through contrast enhancement. It has been proven in previous reports that these multi-layer coated magnetic nanoparticles have superior imaging characteristics over Feridex IV® formulations [28].

3.4. Drug Delivery 3.4.1. F127250 Formulation Lowers Protein Binding Characteristic.

Figure 5:
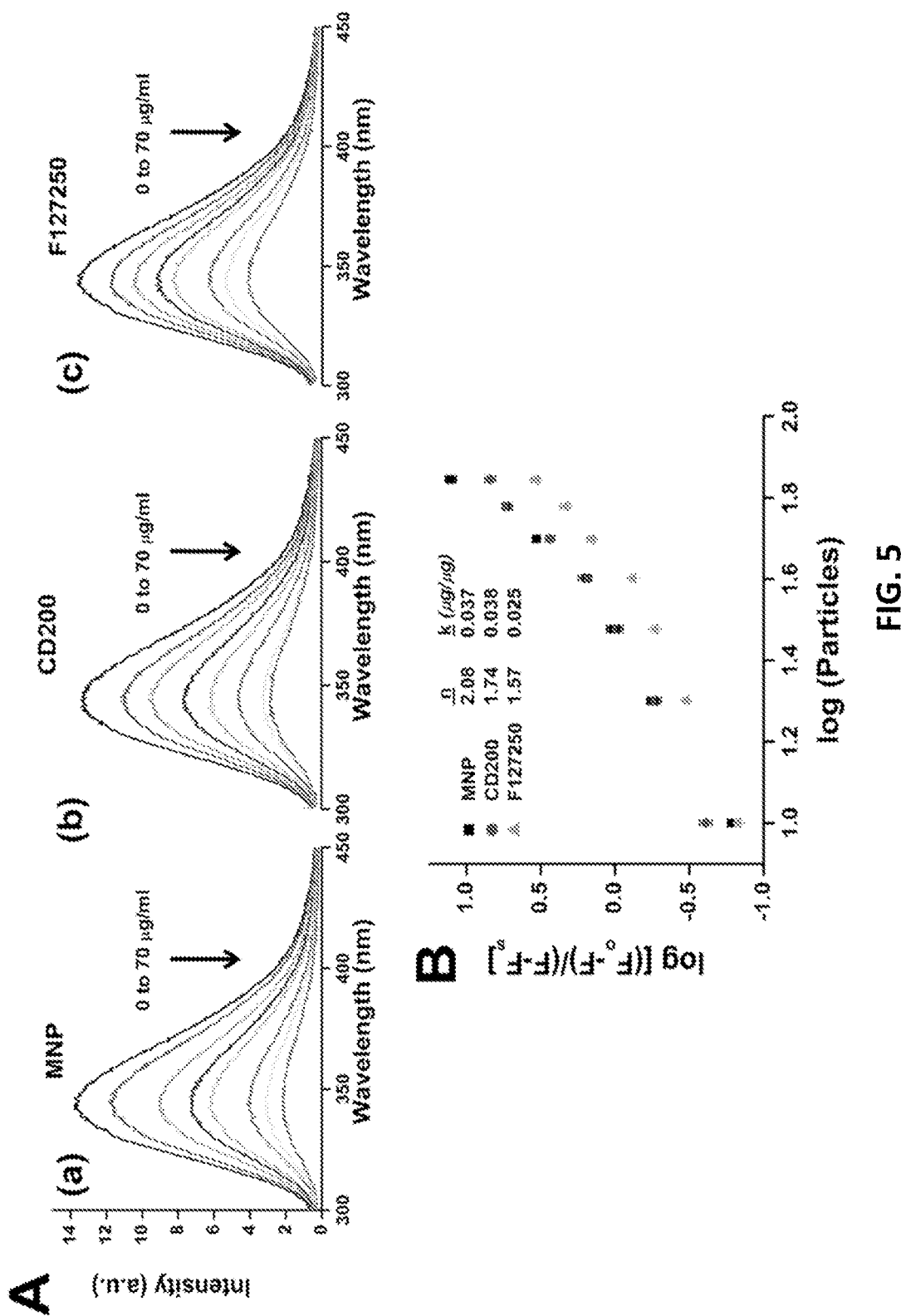
FIG. 5. (A) BSA protein interaction with magnetic nanoparticle (MNP) formulations. Fluorescence emission spectra of BSA solution with various concentrations (0-70 µg) of nanoparticles (a) MNP, (b) CD200, and (c) F127250 at room temperature. (B) Binding constant (k) and number of binding sites calculation graph from fluorescence spectral data. $F_o$, $F$ and $F_s$ are the relative fluorescence emission intensity of BSA alone, in the presence of nanoparticles, and infinity saturated nanoparticles, respectively. Data is a mean of three replicates.

One major shortcoming of the magnetic nanoparticles is their destabilization following adsorption of plasma proteins which leads to nonspecific uptake by the reticulum-endothelial system (RES). To evade clearance by RES and avoid agglomeration, and to improve the circulation time of particles, iron oxide nanoparticles (MNP) were coated with CD (CD100) or CD and F127 polymers (F127250). This coating process led to composite heterogeneous particles composed of an iron oxide inner core with a modifying CD or CD-F127 outer coating. Agglomeration is prevented by the firm coating, emulsifying and adhesive properties of F127 efficiently. To prove this concept, our formulations were tested for in vitro protein adsorption (BSA) in 1×PBS solutions. The BSA adsorption was measured by the dimension of fluorescence of tryptophan residue of BSA. It was noticed that fluorescence intensity reduced with increase of particle addition to BSA solution (FIG. 5A). This reduction is probably dependent upon the formulation. The order of reduction was found to be MNP>CD200>F127250 formulation. From this data, the number of binding sites (n) and binding constant (k) were calculated for each formulation presented in FIG. 5B. It was found that F127250 has a low number of binding sites and binding constant (n=1.57 and k=0.025 µg/µg) while CD200 and MNP formulations have n=1.74 and 2.08, k=0.037 µg/µg and 0.038 µg/µg, respectively. These analyses suggest that the F127250 formulation will have greater circulation time than remaining formulations due to its number of binding sites and lower binding constant [28]. Therefore, in the next section we have evaluated the internalization efficacy of F127250 formulation to determine its utility as a drug delivery carrier.

3.4.2. F127250 Formulation Intracellular Uptak.

Figure 6:
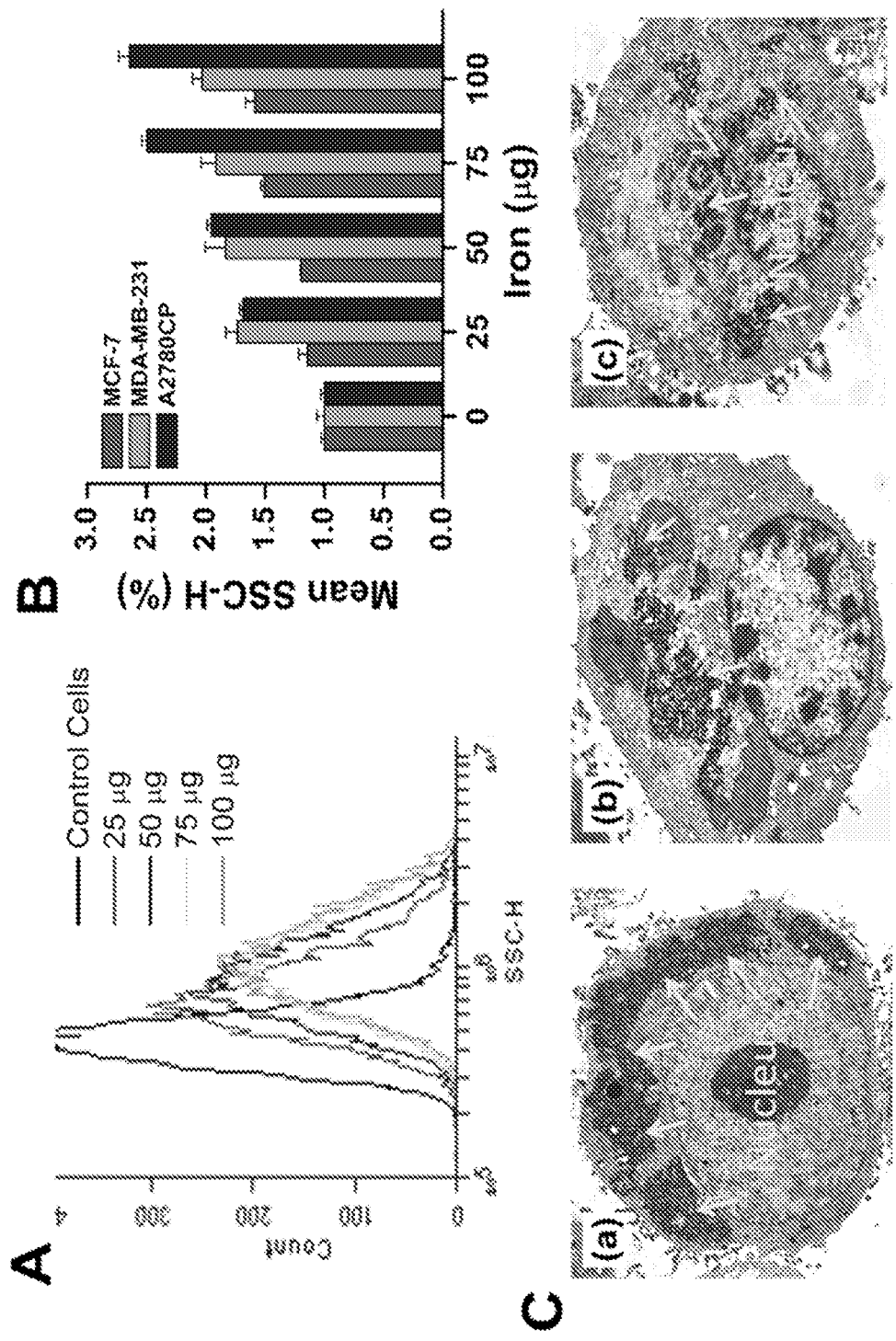
FIG. 6. Cellular uptake of magnetic nanoparticle formulations in cancer cells. (A) Side scattered measurements of nanoparticles uptake by cancer cells using FACS. (B) The quantitative internalization of magnetic nanoparticle formulations in A2780CP (cisplatin resistant ovarian cancer cells), MDA-MB-231 (metastatic breast cancer cells) and MCF-7 (non-metastatic breast cancer cells) are based on the side scattered fluorescence height values. Data represents mean of 3 repeats for each treatment. (C) Transmission electron micrographs of F127250 nanoparticle uptake in (a) A2780CP, (b) MDA-MB-231 and (c) MCF-7 cancer cells. Arrow points indicate F127250 nanoparticles internalization with a distinct contrast.

Intracellular uptake of nanoparticles improves therapeutic outcome because the internalized nanoparticles containing drug are retained in cancer cells. Higher internalization is an index for more accumulation of drug molecules, which release slowly and have sustained effects on cancer cells. We have evaluated our formulations for cellular uptake in three different cancer cells (A2780CP, MDA-MB-231, and MCF-7) by using Flow Cytometeric (Fluorescence activated cell shorter, FACS) analysis [32, 38, 49]. Particles uptake by cancer cells leads to shifting in the side scattered (SSC) height in the Flow Cytometeric analysis. An increased uptake was noticed with increased amount of nanoparticles (0-100 µg) incubated for internalization (FIG. 6A, black to green). The qualitative estimation of particles uptake by various cancer cells demonstrates higher uptake by cisplatin resistant ovarian cancer cells (A2780CP) compared to MCF-7 and MDA-MB-231 breast cancer cells at all the concentrations (FIG. 6B). The order of particles uptake by cancer cells is A2780CP>MDA-MB-231>MCF-7. This phenomenon is clearly observed in the transmission electron microscopy particle uptake experiments (FIG. 6C). A large portion of magnetic nanoparticles (F127250) are accumulated in the epithelial membrane, endoplasmic reticulum, golgi and cytosolic of A2780CP cancer cells. The particles aggregation is also observed in MDA-MB-231 at a few spots. Compared to A2780 and MDA-MB-231 cells, less uptake/accumulation of particles was observed in MCF-7 (non-metastatic) cells. This data demonstrate that our nanoparticles are capable of internalizing within 6 hrs, even in resistant and metastatic cancer cells. In addition, we have also observed that the magnetic nanoparticles uptake in A2780CP cancer cells is relatively higher compared to our recently fabricated PLGA nanoparticles [49].

3.4.3. Internalization of Formulations in Macrophage and A2780CP Ovarian Cancer Cell.

A drug delivery carrier must be present in the blood stream for an appropriately long time to reach and accumulate at its therapeutic site. The opsonization/phagocytosis or removal of drug delivery vehicles from the body by a mononuclear phagocytic system which is also known as the reticuloendothelial system (RES) is a major obstacle to achieving efficient drug delivery. Knowledge on how to design particles to escape phagocytosis could help to overcome this limitation. The macrophages of the mononuclear phagocytic system have the capability to drain nanoparticles from the circulation within seconds. In other words, lower uptake of particles by macrophages determines their efficient use for the drug delivery applications. Therefore, we compared the uptake (indication of phagocytosis) efficiency of MNP, CD200 and F127250 formulations in RAW 264.7 (Mouse leukaemic monocyte macrophage cell line) as determined by Yallapu et al. [27]. Our MNP and CD200 formulations exhibited a greater level of phagocytosis (uptake) compared to the F127250 formulation (FIG. 7A) at two concentrations (50 and 100 µg/ml). The reason for lower phagocytosis of the F127250 formulation is probably due to the protective coating of F127 polymer (pluronic) which helps to form stable nanoparticles in aqueous media. Altogether, these observations reveal clear differences in the phagocytosis pattern of different particles. The lower macrophage uptake of F127250 formulation suggests that this would be a better choice for drug delivery application.

Figure 7:
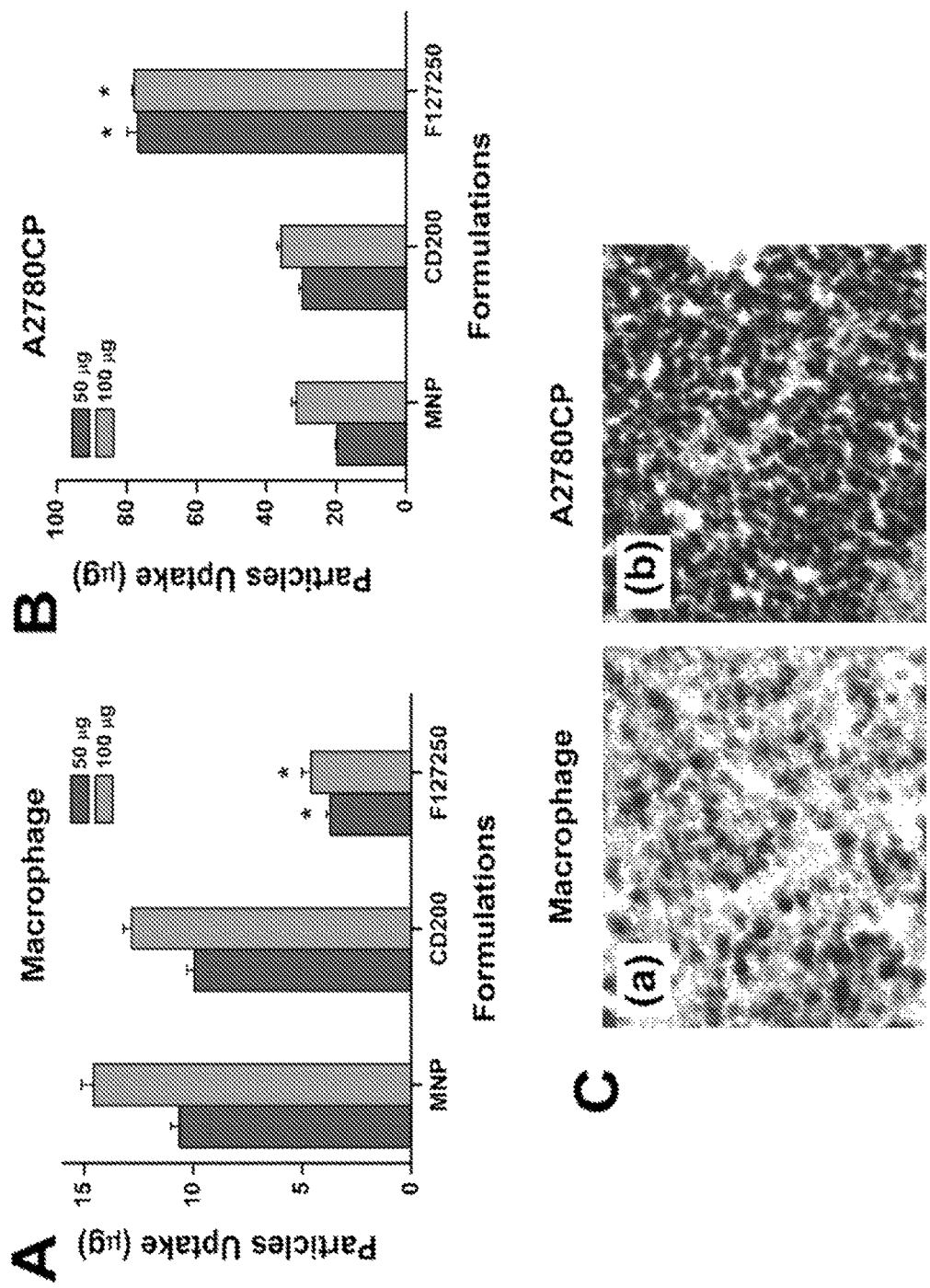
FIG. 7. Quantitative estimation of magnetic nanoparticle formulations in (A) macrophage cells (RAW 264.7 Mouse leukaemic monocyte macrophage cell line) and (B) A2780CP cancer cells. Data indicates mean of 3 repeats for each treatment. (C) Transmission electron micrographs of F127250 nanoparticle uptake in (a) macrophage cells and (b) A2780CP cancer cells.

Next, we monitored the internalization of MNP, CD200, and F127250 formulations with respect to 50 and 100 µg dosages (FIG. 7B) in A2789CP metastatic ovarian cancer cells. The entry of MNP, CD200, and F127250 formulations into the cancer cells was determined [27] and it is varied in different formulations. Evidently, with increase of dose, their uptake is increased. The cellular uptake of the nanocarriers is mainly dependent upon the route of entry, i.e., endocytosis or phagocytosis. Phagocytosis is considered when the particles size was above 300 nm [8, 14, 19]. Whereas endocytic pathways for nanocarriers are subdivided into four categories: namely, clathrin-mediated endocytosis, caveolae-mediated endocytosis, macropinocytosis, and clathrin- and caveolae-independent endocytosis [8, 14, 19]. Taken together, our studies suggest that the internalization of F127250 formulation is 5% in macrophages and is >75% in cancer cells, indicating uptake is based on endocytosis but not phagocytosis (FIG. 7A-B). This phenomenon is also evident in the TEM analysis of particles uptake in macrophage and A2780CP cancer cells (FIG. 7C). A large number of F127250 nanoparticles can be seen inside the A2780CP cancer cells but not in macrophages (RAW 264.7).

3.4.4. CUR Encapsulated F127250 Formulation Anticancer Efficac.

Figure 8:
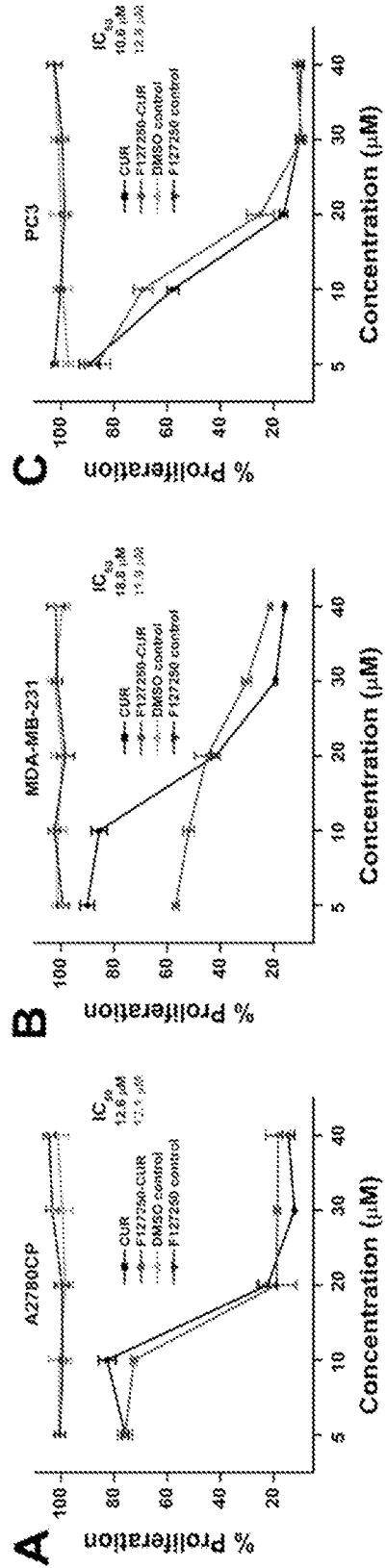
FIG. 8. Anti-proliferative effect of CUR and F127250-CUR treatment in (A) ovarian (A2780CP), (B) breast (MDA-MB-231), and (C) prostate (PC3) cancer cells. Cells were treated with cUR or F127250-CUR in solution, medium was changed on day 2 and cell viability was measured using MTT assay using UV-vis spectrophotometer at 492 nm. Data is mean±SEM (n=6). DMSO and F127250 control did not show any effect at these concentrations.

The therapeutic efficacy of curcumin encapsulated F127250 was evaluated in three different cancer cell lines (A2780CP: ovarian, MDA-MB-231: breast, and PC3: prostate) by MTS cell viability assay [38]. All the studied cell lines have shown typical dose dependant anti-proliferative effects (5-40 µM) by both native curcumin and curcumin encapsulated F127250 formulation (FIG. 8). The control (DMSO or F127250) treatments did not show any effects on cell growth. The in vitro 50% cell growth inhibitory concentration ($IC_{50}$) is the quantitative measure for the cell toxicity induced by chemotherapeutic drug. The $IC_{50}$ values were 12.6, 18.8 and 10.6 µM with curcumin and 12.1, 11.9, and 12.8 µM with curcumin encapsulated F127250 formulation, for A2780CP, MDA-MB-231 and PC3 cancer cells, respectively. This data demonstrates that F127250 containing curcumin is equally efficient in suppressing cell growth even though the release is only 40 percent of nanoformulations within the 48 hour treatment time. Therefore, we can consider that inhibition of cell proliferation is more effective and sustained for long period of times.

Figure 9:
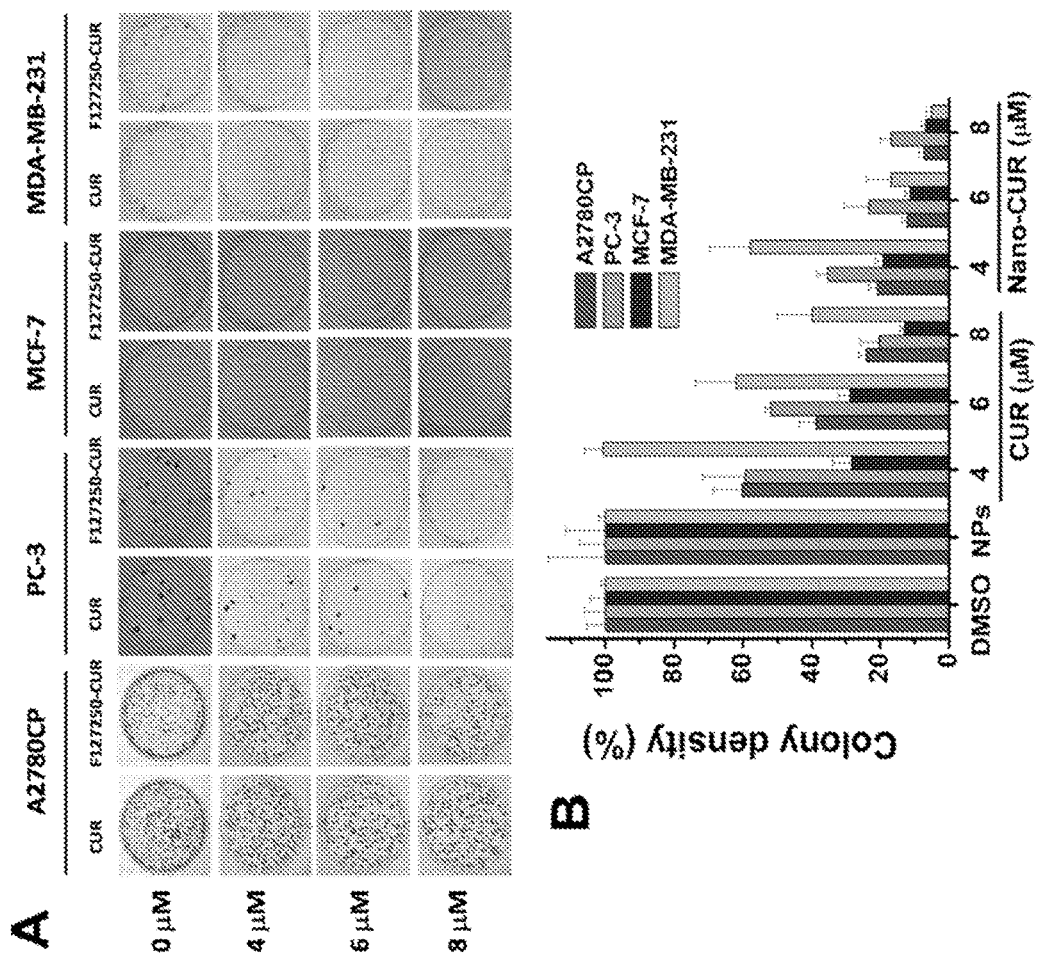
FIG. 9. (A) Representative photographs of colony formation assays of prostate cancer cells (PC3) treated with CUR or F127250-CUR. (B) Quantitation of colony densities in CUR and F127250-CUR treatment groups in three prostate cancer cell lines. Data represent mean of 3 repeats for each treatment, mean±SEM (n=3). DMSO and F127250 control did not show any effect at these concentrations.

Previous literature suggests that colony formation assay provides the ability to evaluate long-term anti-cancer efficacy of the developed drug(s) or drug(s) formulations. To prove our MNP curcumin formulation has greater effects in long term anti-cancer efficacy assays, we have studied free CUR and F127250 curcumin formulation in A2780CP, MDA-MB-231 and PC3 cancer cell lines at equivalent doses 4, 6, and 8 µM. Equivalent quantities of DMSO or F127250 formulations were used as controls for CUR and F127250 CUR formulation, respectively. A significant (p<0.05) decrease in the density of colonies was observed with F12725 curcumin formulation compared to free curcumin (FIG. 9). For example, at 4 µM, F127250 CUR formulation showed 38, 52, 21 and 56% colony densities, whereas free curcumin showed 59, 58, 30, and 100% colony densities after 10 day treatment in A2780CP, MDA-MB-231, and PC3 cancer cells, respectively. The lower colonies indicate an improved therapeutic efficacy of F127250 CUR formulation, resulting from an intracellular uptake effect and sustained release properties.

3.4.5. Molecular Pathwa.

Figure 10:
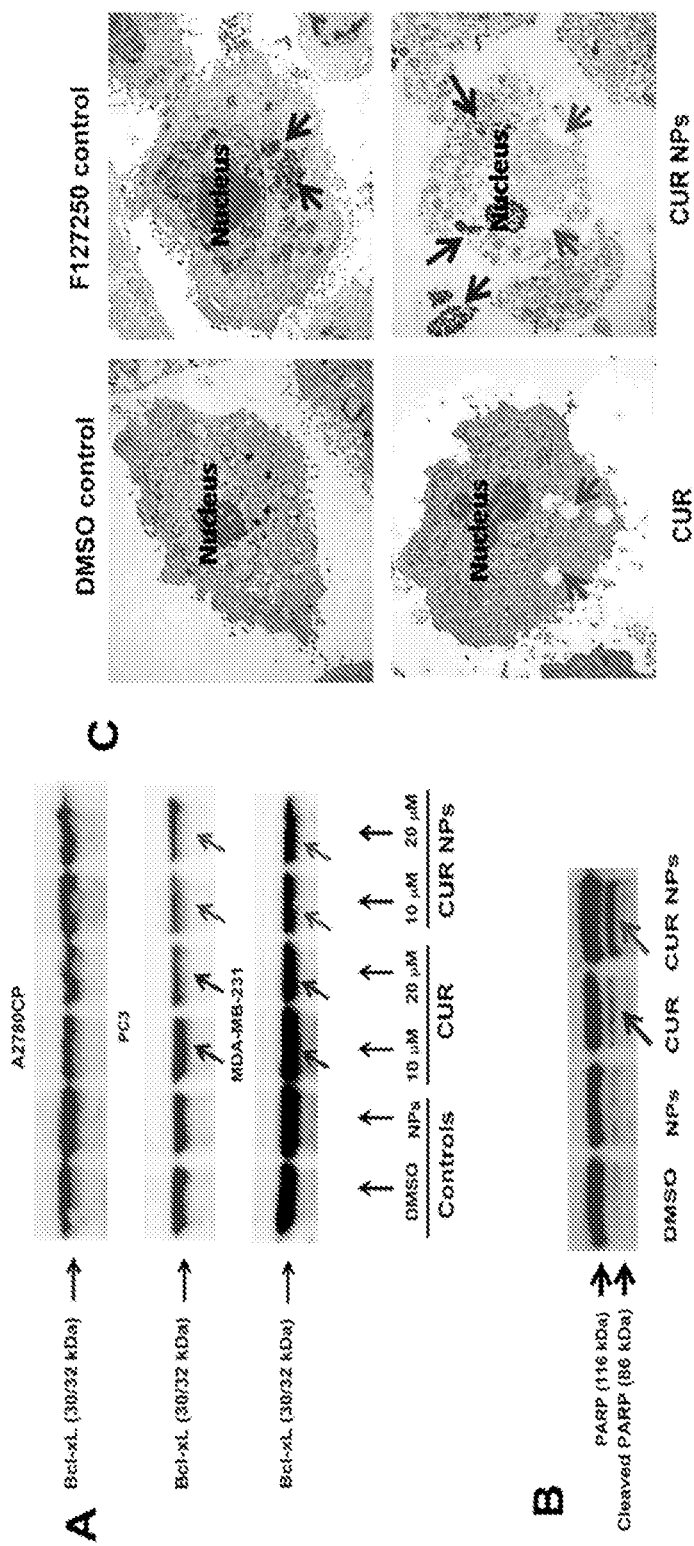
FIG. 10. (A-B) Immunoblot analysis for Bcl-xL expression and PARP cleavage in CUR or F127250-CUR cancer cells. Note: F127250-CUR has shown a decrease in Bcl-xL expression compared to free curcumin (CUR) which indicates reduced cell survival. F127250-CUR has also shown enhanced PARP cleavage compared to free CUR. (C) Ultrastructural cellular changes induced by CUR or F127250-CUR treatments.

Bcl-xl is a transmembrane molecule in the mitochondria. It is one of several anti-apoptotic proteins which are members of the Bcl-2 family of proteins. It has been implicated in the survival of cancer cells [33, 64, 65]. The expression level analysis suggests strong suppression of Bcl-xL expression after treatment with 10 or 20 µM F127250-CUR compared to equivalent amounts of CUR, DMSO and F127250. This data demonstrate less cancer cell survival with the F127250-CUR formulation compared to CUR treatment (FIG. 10A). No change in Bcl-xL expression was observed with control (DMSO and F127250 formulation) treatments. From this study, it was clear that F127250-CUR at 10 and 20 µM exhibited less cancer cell survival and implies induction of apoptosis or cancer cell death. To study its apoptosis, we have investigated the pattern of Poly(ADP-ribose) polymerase (PARP) cleavage which is a protein involved in a number of cellular processes including DNA repair and cell death [66, 67]. Cleavage of PARP is an indicator of DNA damage and apoptosis in response to a diverse range of cytotoxic agents. Because of good PARP expression and its cleavage in response to stress signal, we have chosen PC3 cells for PARP apoptosis assay. PC3 cells treated with 20 µM CUR or equivalent amounts of F127250-CUR exhibited considerable cleavage of full length PARP (116 kDa) into cleaved PARP (86 kDa), which indicates the cancer cells are undergoing cell death via apoptosis pathway (FIG. 10B). The PARP cleavage caused by F127250-CUR formulation is much stronger compared to pure CUR treatment, which suggests an improved efficacy of F127250-CUR formulation for cancer therapy.

The variation of ultrastructural changes in the cancer cells upon exposure to control (DMSO and F127250 formulation), 20 µM CUR or 20 µM F127250-CUR were observed by transmission electron microscopy (TEM) analysis. The control treatments did not cause any ultrastructural changes in PC3 cancer cells (FIG. 10C (a-b)), but both F127250-CUR and 20 µM CUR treated cells demonstrated the formation of endosomal-lysosomal-vacules, which is an indication of cell death (FIG. 10C (c-d). However, this effect was more pronounced in F127250-CUR treated cells, suggesting its improved therapeutic efficacy (FIG. 10C (d)). The vacuole formation is usually caused by the destabilization of subcellular organelle, mitochondrial swelling, opening of the permeability, dissipation of the mitochondrial potential which is a hallmark of typical apoptosis. The internalization of the F127250-CUR and sustained release of active curcumin in the cells probably enhanced the apoptosis in cancer cells, which as a result, further improved therapeutic efficacy of our formulation.

3.5. Toxicity Evaluatio.

Figure 11:
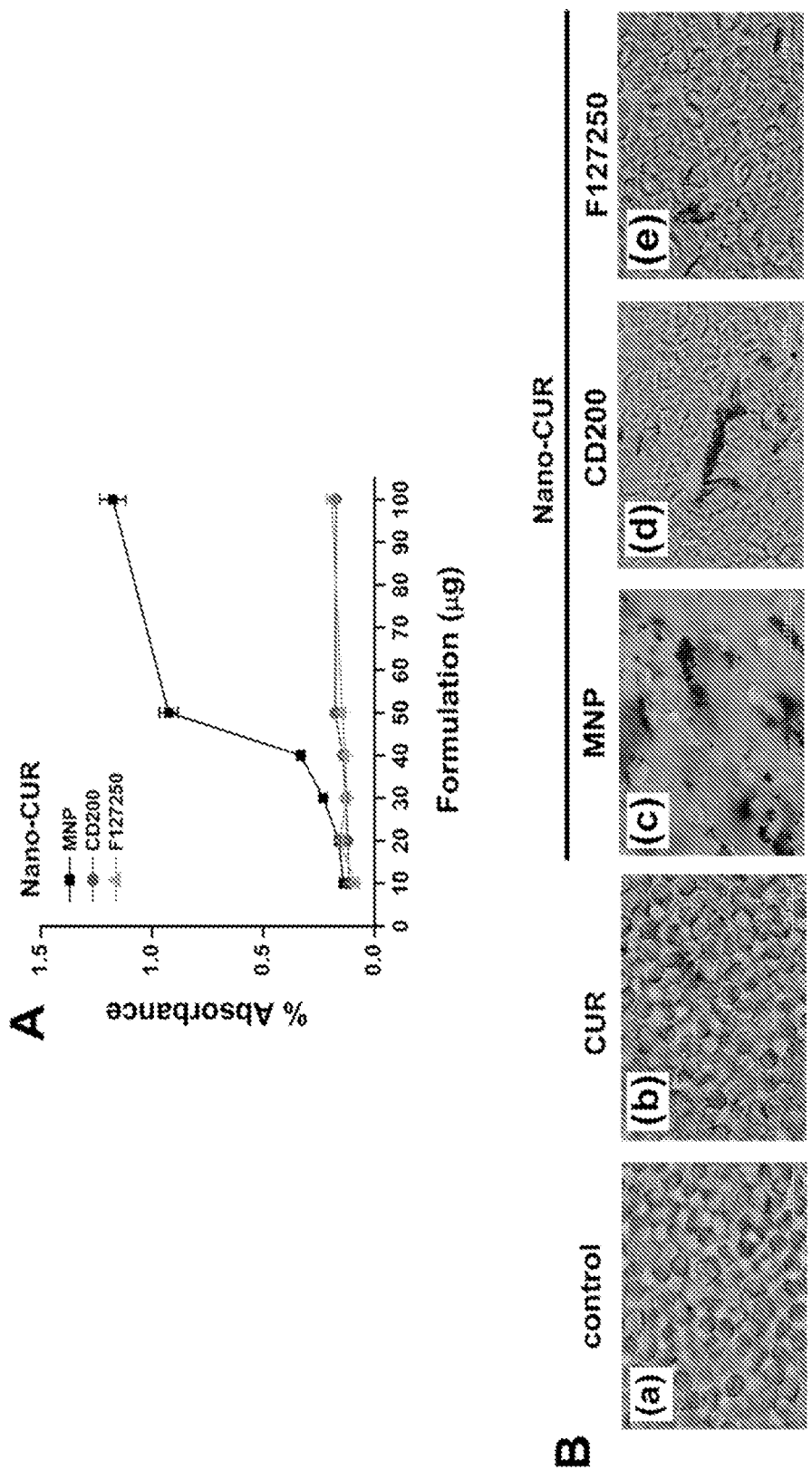
FIG. 11. Haemo-compatibility of CUR containing magnetic nanoparticle (nano-CUR) formulations. (A) nano-CUR formulations were incubated with red blood cells for 2 hrs, centrifuged and supernatant absorbance at 570 nm in UV-vis spectrophotometer was recorded. Controls: magnetic nanoparticles (without curcumin) showed results similar to F127250-CUR formulation (data not shown). Note: MNP formulation shows toxicity on red blood cells because of deposition towards greater aggregation. (B) Red blood cells morphology after incubation with different formulations: (a) control, (b) CUR, (c) MNP (d) CD200, and (e) F127250.

In general, nanoparticles have extremely fast systemic translocation rates following in vivo administration. Blood is one of the common translocation routes to organs for any nanoparticle-mediated therapy. Thus, we want to evaluate our CUR encapsulated F127250 formulation for haemocompatibility. For this, different concentrations (10-100 µg) of CUR containing MNP, CD200, and F127250 formulations were incubated in 100 µl of human blood for 2 hrs. OD measurements recorded on a UV-vis spectrophotometer at $\lambda_{max}$ 570 nm indicate both CUR containing CD200 and F127250 formulations are haemocompatible but CUR containing MNP formulation is toxic after a concentration of 30 μg (FIG. 11A). A similar observation can be found with the red blood cells morphology studies (FIG. 11B). Data in FIG. 11B(a-b) shows a clear morphology of red blood cells without any particles. After 2 hrs of MNP-CUR particles exposure to red blood cells, a rigorous change in the morphology and a higher amount of deposition of particles were noticed (FIG. 11B(c)). Other CUR containing formulations (CD200 and F127250) showed slight deposition of particle clumps; however, no change in the morphology of red blood cells was noted (FIG. 11B(d-e)). In conclusion, F127250-CUR formulation is haemocompatible. The possible reason for diminished haemolytic activity or haemocompatibility is low toxicity coatings of cyclodextrin and/or pluronic polymer F127. These results are consistent with reported nanoparticles [68] coated with pluronic polymers which showed almost no toxicity.

3.6 Bioavailabilit.

Figure 13:
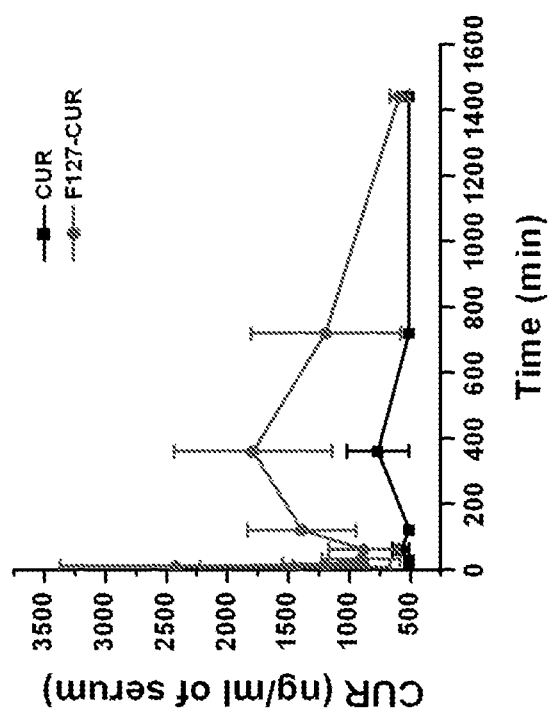
FIG. 13. Bioavailability study: 2000 micro/kg of mice: CUR in Tween 20 or MNP-CUR were injected into nu/nu mice into i.p. and collected blood from tail at different time points (5, 10, 30, 60, 120, 360, 720, and 1440 min). Data represents from 3 mice.

2000 ug/kg of CUR in Tween 20 or MNP-CUR was injected into nu/nu mice i.p. and collected blood from tail at different time points (5, 10, 30, 60, 120, 360, 720, and 1440 min) The data is shown in FIG. 13, and represents data from three mice. These data show that the MNP-CUR formulation provided improved bio-availability compared to free curcumin in the mouse model.

Figure 14:
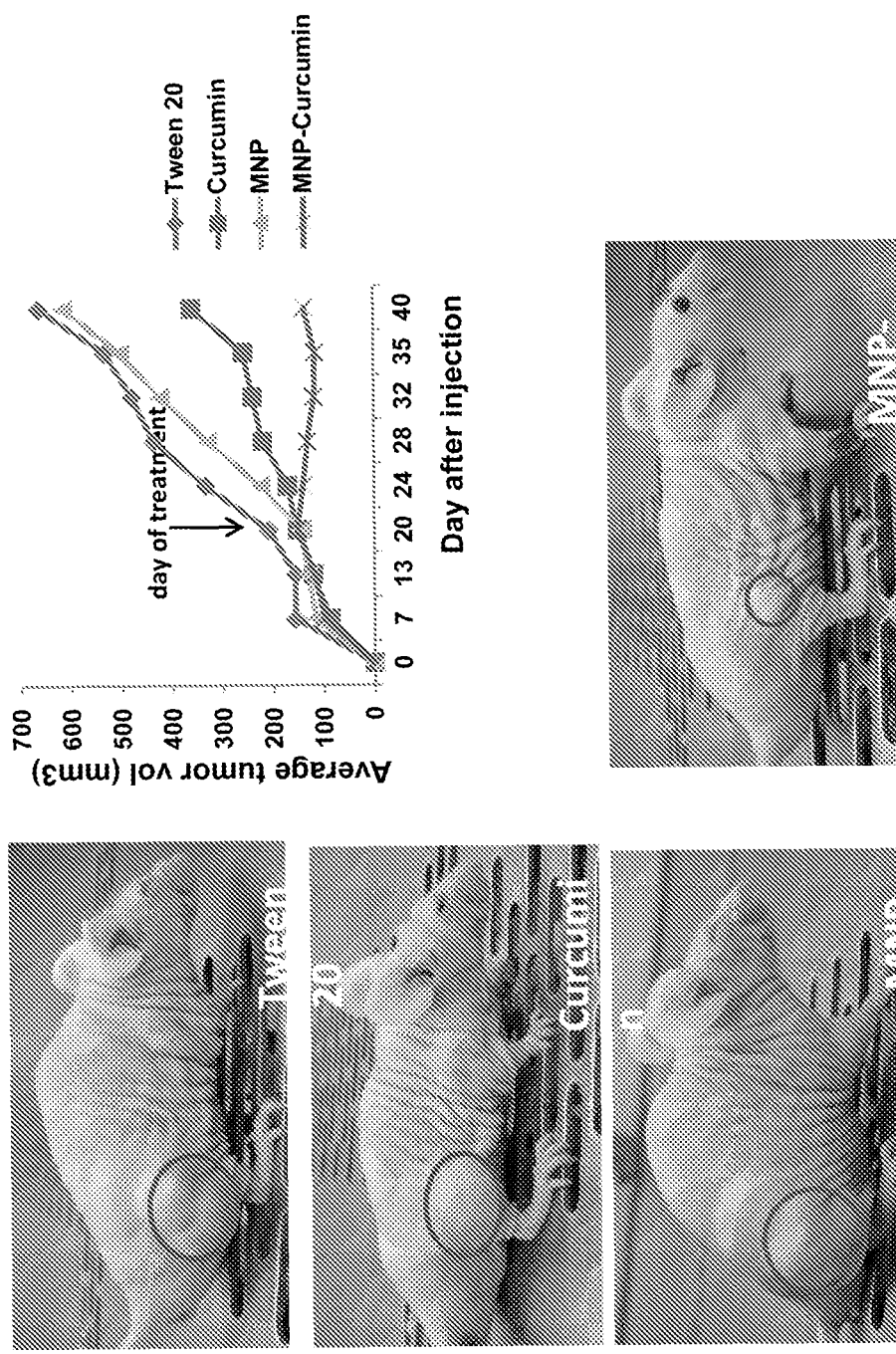
FIG. 14. The effect of MNP-curcumin formulation on pancreatic tumor growth: Pancreatic tumor xenografts were generated in athymic nude mice by subcutaneous (sc) injection of HPAFII human pancreatic cancer cells. Free curcumin or MNP-curcumin formulation was administered intra-tumorally at day 20 post-injection of tumor cells.

We next tested the effect of MNP-curcumin formulation on pancreatic tumor growth: Pancreatic tumor xenografts were generated in athymic nude mice by subcutaneous (sc) injection of HPAFII human pancreatic cancer cells. Free curcumin or MNP-curcumin formulation was administered intra-tumorally at day 20 post-injection of tumor cells. Tumor volume was monitored bi-weekly to determine inhibitory effect of vehicle, free curcumin, blank MNP and MNP-curcumin formulation. These data are presented in FIG. 14, and show that MNP-CUR formulation effectively inhibited the growth of pancreatic tumors in the mouse xenograft model.

We then tested to effect of MNP-curcumin formulation on the expression of Bcl-xL and MCL-1 oncogenes in pancreatic tumor xenografts. Pancreatic tumor xenografts were generated in athymic nude mice by subcutaneous (sc) injection of HPAFII human pancreatic cancer cells. Free curcumin or MNP-curcumin formulation was administered intra-tumorally at day 20 post-injection of tumor cells. Immunohistchemical (IHC) analysis was performed to determine the effect of vehicle (Tween-20), free curcumin, blank MNP and MNP-curcumin formulation on Bcl-xL and MCL-1 oncogenes expression. These data are shown in FIG. 15, and demonstrate that free curcumin and MNP-curcumin formulation reside in the tumor for more than three weeks and effectively inhibited the expression of Bcl-xL and MCL-1 oncogenes in pancreatic tumor xenografts.

4. CONCLUSION

It is essential to develop a tailor made magnetic nanoparticle formulation for multi-functional biomedical applications. A number of magnetic nanoparticle formulations have been generated in the recent past. However, their effective utility has been limited due to higher particle size, loss of magnetization, other inherent properties and lower internalization capacity into the cancer cells which ultimately results in poor therapeutic efficacy in cancer treatment. Our present study illustrates that multi-layer β-cyclodextrin and F127 polymer coated magnetic nanoparticles offer good stability, enhanced cellular uptake, sustained release characteristic of encapsulated anti-cancer drug (curcumin) with improved anti-cancer therapeutic efficacy. The F127250-CUR formulation has shown almost similar growth inhibitory effects as pure curcumin in the cancer cells. The F127250-CUR formulation has also exhibited haemocompatibility, representing an excellent drug delivery approach. On the other hand, recent reports on these types of nanoformulations have shown similar anti-proliferative effects [28, 29, 38, 49] but they do not provide MRI and hyperthermia properties. Additionally, our formulation has shown enhanced molecular effects in cancer cells toward apoptosis.

REFERENCES

[1] Lu A H, Salabas E L, Schuth F. Magnetic nanoparticles: synthesis, protection, functionalization, and application. Angew Chem Int Ed Engl 2007; 46:1222-44.

[2] Ito A, Shinkai M, Honda H, Kobayashi T. Medical application of functionalized magnetic nanoparticles. J Biosci Bioeng 2005; 100:1-11.

[3] Saiyed Z, Telang S, Ramchand C. Application of magnetic techniques in the field of drug discovery and biomedicine. Biomagn Res Technol 2003; 1:2.

[4] Namdeo M, Saxena S, Tankhiwale R, Bajpai M, Mohan Y M, Bajpai S K. Magnetic nanoparticles for drug delivery applications. J Nanosci Nanotechnol 2008; 8:3247-71.

[5] Zhang L, Yu F, Cole A J, Chertok B, David A E, Wang J, et al. Gum arabic-coated magnetic nanoparticles for potential application in simultaneous magnetic targeting and tumor imaging. Aaps J 2009; 11:693-9.

[6] Johannsen M, Gneveckow U, Eckelt L, Feussner A, Waldofner N, Scholz R, et al. Clinical hyperthermia of prostate cancer using magnetic nanoparticles: presentation of a new interstitial technique. Int J Hyperthermia 2005; 21:637-47.

[7] Wilhelm C, Fortin J P, Gazeau F. Tumour cell toxicity of intracellular hyperthermia mediated by magnetic nanoparticles. J Nanosci Nanotechnol 2007; 7:2933-7.

[8] Sun C, Lee J S, Zhang M. Magnetic nanoparticles in MR imaging and drug delivery. Adv Drug Deliv Rev 2008; 60:1252-65.

[9] Kohler N, Sun C, Fichtenholtz A, Gunn J, Fang C, Zhang M. Methotrexate-immobilized poly(ethylene glycol) magnetic nanoparticles for MR imaging and drug delivery. Small 2006; 2:785-92.

[10] Bruce I J, Sen T. Surface modification of magnetic nanoparticles with alkoxysilanes and their application in magnetic bioseparations. Langmuir 2005; 21:7029-35.

[11] Wilhelm C, Gazeau F. Universal cell labelling with anionic magnetic nanoparticles. Biomaterials 2008; 29:3161-74.

[12] Osaka T, Matsunaga T, Nakanishi T, Arakaki A, Niwa D, Iida H. Synthesis of magnetic nanoparticles and their application to bioassays. Anal Bioanal Chem 2006; 384: 593-600.

[13] Dey T. Polymer-coated magnetic nanoparticles: surface modification and end-functionalization. J Nanosci Nanotechnol 2006; 6:2479-83.

[14] Gupta A K, Naregalkar R R, Vaidya V D, Gupta M. Recent advances on surface engineering of magnetic iron oxide nanoparticles and their biomedical applications. Nanomedicine 2007; 2:23-39.

[15] Lee S Y, Harris M T. Surface modification of magnetic nanoparticles capped by oleic acids: characterization and colloidal stability in polar solvents. J Colloid Interface Sci 2006; 293:401-8.

[16] Flexman J A, Minoshima S, Kim Y, Cross D J. Magneto-optical labeling of fetal neural stem cells for in vivo MRI tracking. Conf Proc IEEE Eng Med Biol Soc 2006; 1:5631-4.

[17] Hoehn M, Kustermann E, Blunk J, Wiedermann D, Trapp T, Wecker S, et al. Monitoring of implanted stem cell migration in vivo: a highly resolved in vivo magnetic resonance imaging investigation of experimental stroke in rat. Proc Natl Acad Sci USA 2002; 99:16267-72.

[18] Montet-Abou K, Montet X, Weissleder R, Josephson L. Cell internalization of magnetic nanoparticles using transfection agents. Mol Imaging 2007; 6:1-9.

[19] McCarthy J R, Weissleder R. Multifunctional magnetic nanoparticles for targeted imaging and therapy. Adv Drug Deliv Rev 2008; 60:1241-51.

[20] Guthi J S, Yang S G, Huang G, Li S, Khemtong C, Kessinger C W, et al. MRI-visible micellar nanomedicine for targeted drug delivery to lung cancer cells. Mol Pharm 2010; 7:32-40.

[21] Cinteza L O, Ohulchanskyy T Y, Sahoo Y, Bergey E J, Pandey R K, Prasad P N. Diacyllipid micelle-based nanocarrier for magnetically guided delivery of drugs in photodynamic therapy. Mol Pharm 2006; 3:415-23.

[22] Pradhan P, Giri J, Rieken F, Koch C, Mykhaylyk O, Doblinger M, et al. Targeted temperature sensitive magnetic liposomes for thermo-chemotherapy. J Control Release 142:108-21.

[23] Shubayev V I, Pisanic T R, 2nd, Jin S. Magnetic nanoparticles for theragnostics. Adv Drug Deliv Rev 2009; 61:467-77.

[24] Rubio-Retama J, Zafeiropoulos N E, Serafinelli C, Rojas-Reyna R, Voit B, Cabarcos E L, et al. Synthesis and characterization of thermosensitive PNIPAM microgels covered with superparamagnetic gamma-Fe2O3 nanoparticles. Langmuir 2007; 23:10280-5.

[25] Wang L, Yang Z, Zhang Y, Wang L. Biofunctional nanoparticles with magnetization and luminescence. J Phys Chem C 2009; 113:3955-9.

[26] Guo R, Zhang L, Qian H, Li R, Jiang X, Liu B. Multifunctional nanocarriers for cell imaging, drug delivery, and near-IR photothermal therapy. Langmuir 2010; 26:5428-34.

[27] Yallapu M M, Foy S P, Jain T K, Labhasetwar V. PEG-Functionalized Magnetic Nanoparticles for Drug Delivery and Magnetic Resonance Imaging Applications. Pham Res 2010. DOI: 10.1007/s11095-010-0260-1

[28] Jain T K, Morales M A, Sahoo S K, Leslie-Pelecky D L, Labhasetwar V. Iron oxide nanoparticles for sustained delivery of anticancer agents. Mol Pharm 2005; 2:194-205.

[29] Jain T K, Reddy M K, Morales M A, Leslie-Pelecky D L, Labhasetwar V. Biodistribution, clearance, and biocompatibility of iron oxide magnetic nanoparticles in rats. Mol Pharm 2008; 5:316-27.

[30] Gao J, Gu H, Xu B. Multifunctional magnetic nanoparticles: design, synthesis, and biomedical applications. Acc Chem Res 2009; 42:1097-107.

[31] Banerjee S S, Chen D-H. Magnetic Nanoparticles Grafted with Cyclodextrin for Hydrophobic Drug Delivery. Chem Mater 2007; 19:6345-9.

[32] Bhattarai S R, Kc R B, Kim S Y, Sharma M, Khil M S, Hwang P H, et al. N-hexanoyl chitosan stabilized magnetic nanoparticles: Implication for cellular labeling and magnetic resonance imaging. J Nanobiotechnology 2008; 6:1.

[33] Yallapu M M, Maher D M, Sundram V, Bell M C, Jaggi M, Chauhan S C. Curcumin induces chemo/radio-sensitization in ovarian cancer cells and curcumin nanoparticles inhibit ovarian cancer cell growth. J Ovarian Res 2010; 3:11.

[34] Luo B, Song X J, Zhang F, Xia A, Yang W L, Hu J H, et al. Multi-functional thermosensitive composite microspheres with high magnetic susceptibility based on magnetite colloidal nanoparticle clusters. Langmuir 2010; 26:1674-9.

[35] Beaven G H, Chen S-H, D'albis A, Gratzer W B. A spectroscopic study of the haemin-human-serum-albumin system. Eur J Biochem 1974; 41:539-46.

[36] Chipman D M, Grisaro V, NSharon N. The binding of oligosaccharides containing N-acetylglucosamin and N-acetylmuramic acid to lysozyme. J Biol Chem 1967; 242:4388-94.

[37] Chauhan S C, Vannatta K, Ebeling M C, Vinayek N, Watanabe A, Pandey K K, et al. Expression and functions of transmembrane mucin MUC13 in ovarian cancer. Cancer Res 2009; 69:765-74.

[38] Yallapu M M, Jaggi M, Chauhan S C. beta-Cyclodextrin-curcumin self-assembly enhances curcumin delivery in prostate cancer cells. Colloids Surf B Biointerfaces 2010; 79:113-25.

[39] Bae K H, Ha Y J, Kim C, Lee K R, Park T G. Pluronic/chitosan shell cross-linked nanocapsules encapsulating magnetic nanoparticles. J Biomater Sci Polym Ed 2008; 19:1571-83.

[40] Lim J K, Majetich S A, Tilton R D. Stabilization of superparamagnetic iron oxide core-gold shell nanoparticles in high ionic strength media. Langmuir 2009; 25:13384-93.

[41] Lin J J, Chen J S, Huang S J, Ko J H, Wang Y M, Chen T L, et al. Folic acid-Pluronic F127 magnetic nanoparticle clusters for combined targeting, diagnosis, and therapy applications. Biomaterials 2009; 30:5114-24.

[42] Xiong X Y, Tam K C, Gan L H. Release kinetics of hydrophobic and hydrophilic model drugs from pluronic F127/poly(lactic acid) nanoparticles. J Control Release 2005; 103:73-82.

[43] Dorris A, Rucareanu S, Reven L, Barrett C J, Lennox R B. Preparation and characterization of polyelectrolyte-coated gold nanoparticles. Langmuir 2008; 24:2532-8.

[44] Latham A H, Williams M E. Controlling transport and chemical functionality of magnetic nanoparticles. Acc Chem Res 2008; 41:411-20.

[45] Peracchia M T, Vauthier C, Puisieux F, Couvreur P. Development of sterically stabilized poly(isobutyl 2-cyanoacrylate) nanoparticles by chemical coupling of poly (ethylene glycol). J Biomed Mater Res 1997; 34:317-26.

[46] Gupta A K, Gupta M. Synthesis and surface engineering of iron oxide nanoparticles for biomedical applications. Biomaterials 2005; 26:3995-4021.

[47] Billotey C, Wilhelm C, Devaud M, Bacri J C, Bittoun J, Gazeau F. Cell internalization of anionic maghemite nanoparticles: quantitative effect on magnetic resonance imaging. Magn Reson Med 2003; 49:646-54.

[48] Smirnov P. Cellular magnetic resonance imaging using superparamagnetic anionic iron oxide nanoparticles: applications to in vivo trafficking of lymphocytes and cell-based anticancer therapy. Methods Mol Biol 2009; 512:333-53.

[49] Yallapu M M, Gupta B K, Jaggi M, Chauhan S C. Fabrication of curcumin encapsulated PLGA nanoparticles for improved therapeutic effects in metastatic cancer cells. J Colloid Interface Sci 2010.

[50] Salomir R, Vimeux F C, de Zwart J A, Grenier N, Moonen C T. Hyperthermia by MR-guided focused ultrasound: accurate temperature control based on fast MRI and a physical model of local energy deposition and heat conduction. Magn Reson Med 2000; 43:342-7.
[51] Salomir R, Palussiere J, Vimeux F C, de Zwart J A, Quesson B, Gauchet M, et al. Local hyperthermia with MR-guided focused ultrasound: spiral trajectory of the focal point optimized for temperature uniformity in the target region. J Magn Reson Imaging 2000; 12:571-83.
[52] Le Renard P E, Jordan O, Faes A, Petri-Fink A, Hofmann H, Rufenacht D, et al. The in vivo performance of magnetic particle-loaded injectable, in situ gelling, carriers for the delivery of local hyperthermia. Biomaterials 2010; 31:691-705.
[53] Le Renard P E, Buchegger F, Petri-Fink A, Bosman F, Rufenacht D, Hofmann H, et al. Local moderate magnetically induced hyperthermia using an implant formed in situ in a mouse tumor model. Int J Hyperthermia 2009; 25:229-39.
[54] Gentilini C, Evangelista F, Rudolf P, Franchi P, Lucarini M, Pasquato L. Water-soluble gold nanoparticles protected by fluorinated amphiphilic thiolates. J Am Chem Soc 2008; 130:15678-82.
[55] Latorre M, Rinaldi C. Applications of magnetic nanoparticles in medicine: magnetic fluid hyperthermia. P R Health Sci J 2009; 28:227-38.
[56] Duguet E, Vasseur S, Mornet S, Devoiselle J M. Magnetic nanoparticles and their applications in medicine. Nanomedicine 2006; 1:157-68.
[57] Xia H-B, Yi J, Foo P-S, Liu B. Facile fabrication of water-soluble magnetic nanoparticles and their spherical aggregates. Chem Mater 2007; 19:4087-91.
[58] Kato H, Ishida T. Present and future status of noninvasive selective deep heating using RF in hyperthermia. Med Biol Eng Comput 1993; 31 Suppl:S2-11.
[59] Motoyama J, Hakata T, Kato R, Yamashita N, Morino T, Kobayashi T, et al. Size dependent heat generation of magnetite nanoparticles under AC magnetic field for cancer therapy. Biomagn Res Technol 2008; 6:4.
[60] Deger S, Taymoorian K, Boehmer D, Schink T, Roigas J, Wille A H, et al. Thermoradiotherapy using interstitial self-regulating thermoseeds: an intermediate analysis of a phase II trial. Eur Urol 2004; 45:574-9; discussion 80.
[61] Kawashita M, Tanaka M, Kokubo T, Inoue Y, Yao T, Hamada S, et al. Preparation of ferrimagnetic magnetite microspheres for in situ hyperthermic treatment of cancer. Biomaterials 2005; 26:2231-8.
[62] Serrano M C, Portoles M T, Pagani R, de Guinoa J S, Ruiz-Hernandez E, Arcos D, et al. In vitro positive biocompatibility evaluation of glass-glass ceramic thermoseeds for hyperthermic treatment of bone tumors. Tissue Eng Part A 2008; 14:617-27.
[63] Liong M, Lu J, Kovochich M, Xia T, Ruehm S G, Nel A E, et al. Multifunctional inorganic nanoparticles for imaging, targeting, and drug delivery. ACS Nano 2008; 2:889-96.
[64] Orrenius S, Zhivotovsky B. The future of toxicology-Does it matter how cells die? Chem Res Toxicol 2006; 19:729-33.
[65] Malugin A, Kopeckova P, Kopecek J. HPMA copolymer-bound doxorubicin induces apoptosis in ovarian carcinoma cells by the disruption of mitochondrial function. Mol Pharm 2006; 3:351-61.
[66] McGowan A J, Ruiz-Ruiz M C, Gorman A M, Lopez-Rivas A, Cotter T G. Reactive oxygen intermediate(s) (ROI): common mediator(s) of poly(ADP-ribose)polymerase (PARP) cleavage and apoptosis. FEBS Lett 1996; 392:299-303.
[67] de Murcia G, Menissier de Murcia J. Poly(ADP-ribose) polymerase: a molecular nick-sensor. Trends Biochem Sci 1994; 19:172-6.
[68] Liu F, Park J Y, Zhang Y, Conwell C, Liu Y, Bathula S R, Huang L. Targeted cancer therapy with novel high drug-loading nanocrystals. J Pharm Sci 2010; 99:3542-3551.

We claim:

1. A magnetic nanoparticle (MNP) comprising
   (a) a core iron oxide nanoparticle;
   (b) first layer of cyclodextrin bound directly to the iron oxide of the core nanoparticle; and
   (c) a second layer of a poly(ethylene-co-propylene glycol) polymer bound directly to the cyclodextrin layer, wherein the second layer is the outer layer of the MNP.

2. The MNP of claim 1, wherein the core nanoparticle is between about 5 nm and about 30 nm in diameter.

3. The MNP of claim 1, wherein the cyclodextrin is selected from the group consisting of α-cyclodextrin, β-cyclodextrin, and γ-cyclodextrin, and derivatives thereof.

4. The MNP of claim 1, wherein the cyclodextrin comprises β-cyclodextrin, or derivatives thereof.

5. The MNP of claim 1, wherein the MNP comprises a molar ratio of between about 1:40 to 1:300 cyclodextrin:iron ion in the core nanoparticle.

6. The MNP of claim 1, wherein the MNP comprises a molar ratio of between about 1:1 and 1:10 cyclodextrin:poly(ethylene-co-propylene glycol).

7. The MNP of claim 1, wherein the MNP further comprises a therapeutic loaded into the MNP and/or a photosensitizer loaded into the MNP.

8. An MNP cluster, comprising a plurality of MNPs according to claim 1, wherein the MNP cluster is between about 50 nm and about 200 nm in diameter.

9. The MNP cluster of claim 8, wherein the MNP cluster is between about 75 nm and about 150 nm in diameter.

10. A method for making the magnetic nanoparticle (MNP) of claim 1, comprising
    (a) precipitating iron salts in the presence of ammonia to obtain an iron oxide core nanoparticle; and
    (b) coating the iron oxide core nanoparticle with:
       (i) cyclodextrin; and
       (ii) an outer layer of poly(ethylene-co-propylene glycol).

11. The method of claim 10, wherein the cyclodextrin is selected from the group consisting of α-cyclodextrin, β-cyclodextrin, and γ-cyclodextrin, and derivatives thereof.

12. The method of claim 10, wherein the cyclodextrin comprises β-cyclodextrin, or derivatives thereof.

13. The method of claim 10, wherein the MNP comprises a molar ratio of between about 1:40 to 1:300 cyclodextrin: iron ion in the core nanoparticle.

14. The method of claim 10, wherein the MNP comprises a molar ratio of between about 1:1 and 1:10 cyclodextrin: poly(ethylene-co-propylene glycol).

15. The method of claim 10, wherein the method further comprises loading a therapeutic into the MNP and/or loading a photosensitizer into the MNP.

16. A method for drug delivery, comprising administering the MNP of claim 1, wherein a drug is loaded into the MNP, to a subject in need thereof.

17. A method for hyperthermic treatment, comprising
    (a) administering the MNP of claim 1 to a subject in need thereof so as to localize the MNP to the vicinity of a tissue of interest, and
    (b) applying an alternating magnetic field to produce heat from the MNP;

wherein the heat produced from the MNP damages cells in the tissue and/or sensitizes cells in the tissue to other therapy.

18. A method for photodynamic treatment (PDT), comprising
(a) administering the MNP of claim 1, wherein the MNP further comprises a photosensitizer, to a subject in need of PDT; and
(b) applying a light source to excite the photosensitizer;
wherein the excitation of the photosensitizer produces reactive oxygen species that damage cells in the relevant tissue.

19. A method for in vivo imaging comprising
(a) administering the MNP of claim 1 to a subject in need of magnetic resonance imaging; and
(b) conducting magnetic resonance imaging (MRI) on the subject;
wherein the MRI permits in vivo imaging of the relevant tissue.

* * * * *

UNITED STATES PATENT AND TRADEMARK OFFICE
CERTIFICATE OF CORRECTION

| | | |
|---|---|---|
| PATENT NO. | : 9,642,925 B2 | Page 1 of 1 |
| APPLICATION NO. | : 13/884625 | |
| DATED | : May 9, 2017 | |
| INVENTOR(S) | : Subhash Chauhan, Meena Jaggi and Murali Mohan Yallapu | |

It is certified that error appears in the above-identified patent and that said Letters Patent is hereby corrected as shown below:

In the Specification

Column 1, please replace Lines 15, 16, 17, and 18 with the following statement:
-- This invention was made with Government support under Grant Number
W81XWH-14-1-0154 awarded by the U.S. Army and CA162106 and CA142736 awarded by
the National Institutes of Health. The Government has certain rights in the invention. --

Signed and Sealed this
Eleventh Day of September, 2018

Andrei Iancu
*Director of the United States Patent and Trademark Office*